United States Patent
Flaherty et al.

(10) Patent No.: US 6,699,218 B2
(45) Date of Patent: Mar. 2, 2004

(54) TRANSCUTANEOUS DELIVERY MEANS

(75) Inventors: J. Christopher Flaherty, Topsfield, MA (US); John T. Garibotto, Charlestown, MA (US)

(73) Assignee: Insulet Corporation, Beverly, MA (US)

( * ) Notice: Subject to any disclaimer, the term of this patent is extended or adjusted under 35 U.S.C. 154(b) by 0 days.

(21) Appl. No.: 10/037,902

(22) Filed: Nov. 9, 2001

(65) Prior Publication Data

US 2002/0123740 A1 Sep. 5, 2002

Related U.S. Application Data

(60) Provisional application No. 60/247,598, filed on Nov. 9, 2000.

(51) Int. Cl.[7] .................... A61M 31/00; A61M 32/00
(52) U.S. Cl. ............................... 604/131; 604/67
(58) Field of Search ................ 604/65–68, 141, 604/326, 180, 132, 153, 142, 20–22, 67

(56) References Cited

U.S. PATENT DOCUMENTS

| | | |
|---|---|---|
| 3,631,847 A | 1/1972 | Hobbs |
| 3,812,843 A | 5/1974 | Wootten et al. |
| 4,067,000 A | 1/1978 | Carlson |
| 4,108,177 A | 8/1978 | Pistor |
| 4,151,845 A | 5/1979 | Clemens |
| 4,211,998 A | 7/1980 | Junginger et al. |
| 4,231,019 A | 10/1980 | Junginger et al. |
| 4,268,150 A | 5/1981 | Chen |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |

(List continued on next page.)

FOREIGN PATENT DOCUMENTS

| | | |
|---|---|---|
| DE | 4200595 | 7/1993 |
| DE | 19920896 | 9/2000 |
| EP | 0342947 | 5/1989 |
| EP | 0763369 | 3/1997 |
| EP | 0867196 | 3/1998 |

(List continued on next page.)

OTHER PUBLICATIONS

US 5,954,699, 9/1999, Jost et al. (withdrawn)
Flaherty et al, Medical Apparatus Remote Control and Method, US Patent PUb No. 2002/0126036, Sep. 12, 2002.*

(List continued on next page.)

Primary Examiner—Brian L. Casler
Assistant Examiner—Roz GhaFoorian
(74) Attorney, Agent, or Firm—McDermott Will & Emery

(57) ABSTRACT

A device for delivering fluid to a patient including a passageway having a proximal fluid transport tube, a distal fluid transport tube, and a tubular expansion member coupling the fluid transport tubes. A penetrating member is positioned within the expansion member for axial movement between the fluid transport tubes, and has a sharpened distal tip. The device also includes a dispenser for causing fluid from a reservoir to flow to the proximal fluid transport tube, a housing containing the dispenser and the passageway and including an exit port receiving the distal fluid transport tube, and a connecting member secured to the penetrating member. The connecting member is movable by a user from an exterior of the housing and arranged such that movement causes the penetrating member to move between an extended position for subcutaneously inserting the distal fluid transport tube into a patient, and a retracted position.

41 Claims, 16 Drawing Sheets

U.S. PATENT DOCUMENTS

| | | |
|---|---|---|
| 4,514,732 A | 4/1985 | Hayes, Jr. |
| 4,529,401 A | 7/1985 | Leslie et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| D303,013 S | 8/1989 | Konopka |
| 4,855,746 A | 8/1989 | Stacy |
| 4,882,600 A | 11/1989 | Van de Moere |
| 4,886,499 A | 12/1989 | Cirelli et al. |
| 4,898,579 A | 2/1990 | Groshong et al. |
| 4,969,874 A | 11/1990 | Michel et al. |
| 4,973,998 A | 11/1990 | Gates |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,176,662 A | 1/1993 | Bartholomew et al. |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,242,406 A | 9/1993 | Gross et al. |
| 5,244,463 A | 9/1993 | Cordner, Jr. et al. |
| 5,254,096 A | 10/1993 | Rondelet et al. |
| 5,257,980 A | 11/1993 | Van Antwerp et al. |
| 5,281,202 A | 1/1994 | Weber et al. |
| 5,312,337 A | 5/1994 | Flaherty et al. |
| 5,318,540 A | 6/1994 | Athayde et al. |
| 5,342,313 A | 8/1994 | Campbell et al. |
| 5,411,480 A | 5/1995 | Kriesel |
| 5,433,710 A | 7/1995 | Van Antwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,507,288 A | 4/1996 | Bocker et al. ............... 128/633 |
| 5,514,096 A | 5/1996 | Hiejima |
| 5,533,389 A | 7/1996 | Kamen et al. |
| 5,545,152 A | 8/1996 | Funderburk et al. |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,660,728 A | 8/1997 | Saaski et al. |
| 5,665,065 A | 9/1997 | Colman et al. |
| 5,665,070 A | 9/1997 | McPhee |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson |
| 5,800,405 A | 9/1998 | McPhee |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,991 A | 12/1998 | Gross et al. |
| 5,851,197 A | 12/1998 | Marano et al. |
| 5,858,005 A | 1/1999 | Kriesel |
| D405,524 S | 2/1999 | Falk et al. |
| 5,875,393 A | 2/1999 | Altschul et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,935,099 A | 8/1999 | Peterson et al. |
| 5,954,058 A | 9/1999 | Flaherty |
| 5,957,890 A | 9/1999 | Mann et al. |
| 5,965,848 A | 10/1999 | Altschul et al. |
| 5,983,094 A | 11/1999 | Altschul et al. |
| 5,993,423 A | 11/1999 | Choi |
| 5,997,501 A * | 12/1999 | Gross et al. ................... 604/65 |
| 6,019,747 A | 2/2000 | McPhee |
| 6,061,580 A | 5/2000 | Altschul et al. |
| 6,071,292 A | 6/2000 | Makower et al. |
| 6,144,847 A | 11/2000 | Altschul et al. |
| 6,152,898 A | 11/2000 | Olsen |
| 6,485,461 B1 * | 11/2002 | Mason et al. ............... 604/132 |

FOREIGN PATENT DOCUMENTS

| | | |
|---|---|---|
| EP | 0937475 | 8/1999 |
| WO | WO81/01658 | 6/1981 |
| WO | WO86/06796 | 11/1986 |
| WO | WO98/00193 | 1/1998 |
| WO | WO98/01071 | 1/1998 |
| WO | WO00/19887 | 9/1999 |
| WO | WO99/62576 | 9/1999 |
| WO | WO99/56803 | 11/1999 |
| WO | WO0010628 | 3/2000 |
| WO | WO00/29047 | 5/2000 |
| WO | WO00/29049 | 5/2000 |
| WO | WO00/74752 | 5/2000 |
| WO | WO00/30705 | 6/2000 |
| WO | WO00/78210 | 6/2000 |
| WO | WO00/48112 | 8/2000 |
| WO | WO00/61215 | 10/2000 |
| WO | WO01/52727 | 1/2001 |
| WO | WO01/5663 | 8/2001 |
| WO | WO01/76684 | 10/2001 |
| WO | WO 02/20073 | 3/2002 |

OTHER PUBLICATIONS

Flaherty et al, Data Collection Assembly for Patient Infusion system, US Patent Pub No. 2002/0040208 Apr. 4, 2002.*

Gross et al, Pre–filled Drug delivery Device and method of manufacture and assembly of same, US Patent Pub No. 2002/0010423, Jan. 24, 2002.*

Web-Site Brochure dated Jan. 4, 2000. MiniMed 508. "Doing its job. Naturally." www.minimed.com/tiles/mm_.htm.

Web-Site Brochure dated Dec. 20, 1999. Applied Medical Technology. "508 Pump Information". www.applied-medical.co.uk/508.htm.

Web-Site Brochure dated Jan. 4, 2000. "The Glucose Sensor". www.animascorp.com/sensor_f.html.

Web-Site Brochure dated Dec. 20, 1999. "The Animas R-1000 Insulin Pump". www.animascorp.com/pump_f_s.html.

Web-Site Brochure dated Dec. 20, 1999. "The Animas R-1000 Insulin Pump". www.animascorp.com/pump_f_f.html.

Web-Site Brochure dated Jan. 4, 2000. SOOIL—Homepage. "Portable Insulin Pump". www.sooil.com/intro2.htm.

Web-Site Brochure dated Jan. 4, 2000. SOOIL—Homepage. "Portable Insulin Pump". www.sooil.com/product2.htm.

Web-Site Brochure dated Jan. 4, 2000. SOOIL—Homepage. "Portable Insulin Pump". www.sooil.com/product3.htm.

Web-Site Brochure dated Jan. 4, 2000. SOOIL—Homepage. "Portable Insulin Pump". www.sooil.com/product4.htm.

* cited by examiner

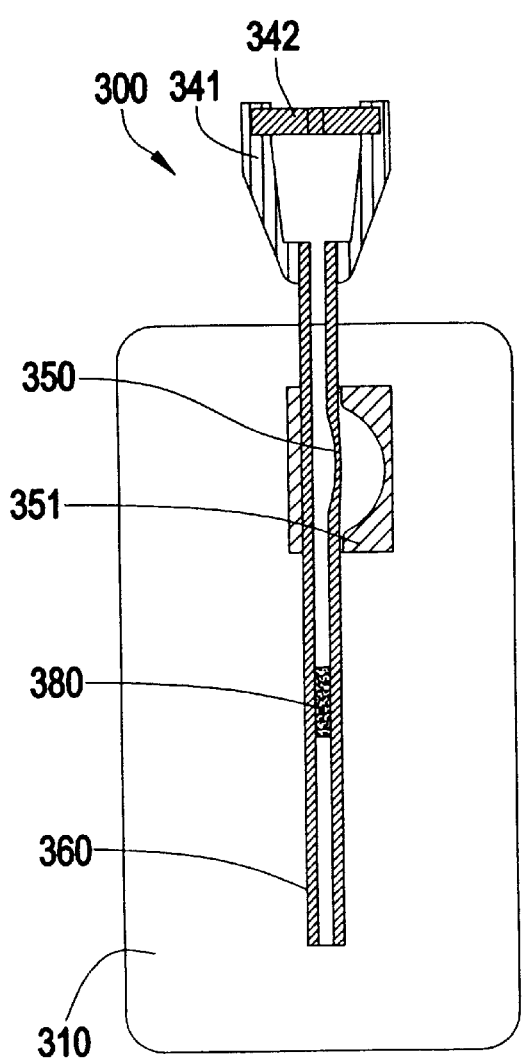
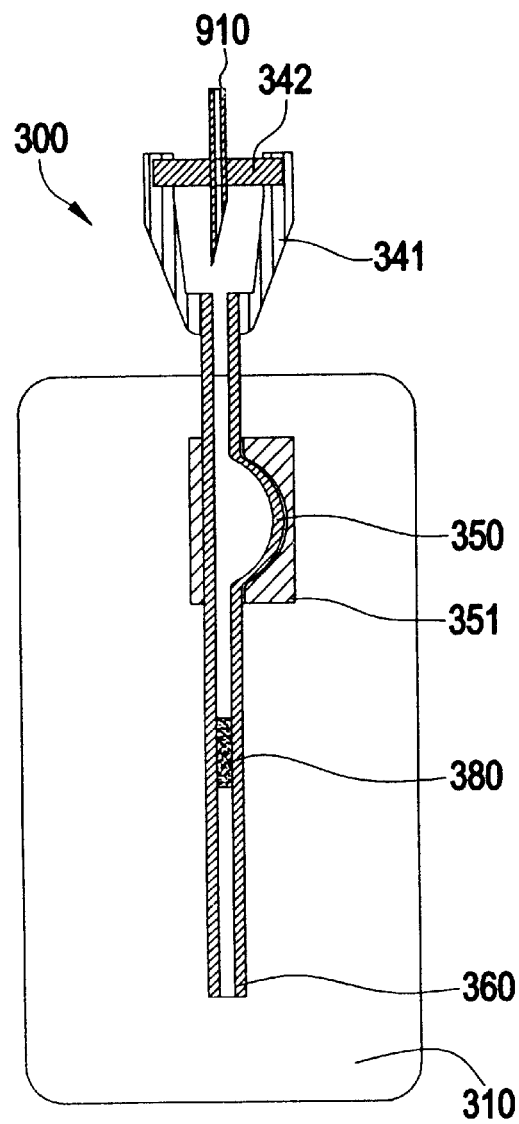

TRANSCUTANEOUS DELIVERY MEANS

CROSS-REFERENCE TO RELATED APPLICATIONS

The present application claims priority to provisional U.S. patent application serial No. 60/247,598, filed on Nov. 9, 2000, which is assigned to the assignee of the present application and incorporated herein by reference. The present application is related to U.S. patent application Ser. No. 09/943,992, filed on Aug. 31, 2001, which is assigned to the assignee of the present application and incorporated herein by reference.

FIELD OF THE INVENTION

The present invention relates generally to devices for delivering therapeutic fluids and more particularly to small, disposable, portable infusion devices and methods that can be used to transcutaneously deliver these fluids safely and simply to a mammalian patient. Even more particularly, the present invention relates a transcutaneous infusion assembly that allows transcutaneous placement of a soft cannula safely and automatically, and does not require the disposal of a sharp, contaminated needle.

BACKGROUND OF THE INVENTION

Today, there are numerous diseases and other physical ailments that are treated by various medicines including pharmaceuticals, nutritional formulas, biologically derived or active agents, hormonal and gene based material and other substances in both solid or liquid form. In the delivery of these medicines, it is often desirable to bypass the digestive system of a mammalian patient to avoid degradation of the active ingredients caused by the catalytic enzymes in the digestive tract and liver. Delivery of a medicine other than by way of the intestines is known as parenteral delivery. Parenteral delivery of various drugs in liquid form is often desired to enhance the effect of the substance being delivered, insuring that the unaltered medicine reaches its intended site at a significant concentration. Also, undesired side effects associated with other routes of delivery, such as systemic toxicity, can potentially be avoided.

Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissue or directly into organs, tumors, cavities, bones or other site-specific locations within the body.

Parenteral delivery of liquid medicines into the body is often accomplished by administering bolus injections using a needle and reservoir, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al.

The ambulatory pumps often work with a reservoir to contain the liquid medicine, such as a cartridge or reservoir, and use electromechanical pumping or metering technology to deliver the medication to the patient via tubing from the infusion device to a needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling these devices can be difficult and require the patient to carry both the intended medication as well as filling accessories. The devices require specialized care, maintenance, and cleaning to assure proper functionality and safety for their intended long-term use. Due to the high cost of existing devices, healthcare providers limit the patient populations approved to use the devices and therapies for which the devices can be used.

Clearly, therefore, there was a need for a programmable and adjustable infusion system that is precise and reliable and can offer clinicians and patients a small, low cost, light weight, simple to use alternative for parenteral delivery of liquid medicines.

In response, the applicant of the present application provided a small, low cost, lightweight, easy to use device for delivering liquid medicines to a patient, which is described in co-pending U.S. application Ser. No. 09/943,992, filed on Aug. 31, 2001. The device includes an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. To reduce the size, complexity and costs of the device, the device is provided with a housing that is free of user input components, such as a keypad, for providing flow instructions to the local processor.

What is still desired are new and improved devices for delivering fluid to a patient. Preferably, the fluid delivery devices will be simple in design, and inexpensive and easy to manufacture, to further reduce the size, complexity and costs of the devices, such that the devices or portions thereof lend themselves to being small and disposable in nature.

In addition, the fluid delivery devices will preferably include a transcutaneous infusion assembly that allows transcutaneous placement of a soft cannula safely and automatically, and does not require the disposal of a sharp, contaminated needle.

SUMMARY OF THE INVENTION

The applicant has determined that a sophisticated ambulatory infusion device that can be programmed to reliably deliver variable flow profiles of liquid medications, yet is small, lightweight and low cost, is needed. Avoiding the general upkeep and maintenance required by expensive, long-term use devices is necessary for broader acceptance of ambulatory infusion therapy. Smaller and lighter devices are easier to carry and are more comfortable for the patient even allowing the device to attach with adhesive to the patient's skin similar to a transdermal patch.

An inexpensive device allows greater flexibility in prescribing the device for use by reducing the financial burden on healthcare insurance providers, hospitals and patient care centers as well as patients themselves. In addition, low cost devices make it more practical for a patient to have one or more replacement devices readily available. If the primary device is lost or becomes dysfunctional, availability of the replacement eliminates costly expedited repair and avoids periods of discontinued ambulatory therapy.

The present invention, therefore, provides a small, lightweight and low cost fluid delivery device capable of adjustable and programmable fluid delivery includes a housing that surrounds a reservoir chamber. In fluid communication with the reservoir chamber is a dispenser for dispensing the fluid from the reservoir in finite amounts. The dispenser is controlled by an electronic microcontroller (referred to as the "local processor") of the fluid delivery device. The fluid delivery device further includes a communication element that receives information from a remote control device not mechanically attached to the fluid delivery device of the present invention. Also included is an exit port assembly in fluid communication with the dispenser from which the liquid medication exits the fluid delivery device and enters the body of a mammalian patient transcutaneously.

The types of liquids that could be delivered by the fluid delivery device of the present invention include but are not limited to: insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device of the present invention might be used to treat are diabetes, cardiovascular disease, pain, chronic pain, cancer, AIDS, neurological diseases, Alzheimer's Disease, ALS, Hepatitis, Parkinson's Disease or spasticity.

The housing of the fluid delivery device is preferably free of electromechanical elements, such as switches or buttons, that the patient would press to program or alter the programming of the fluid delivery device. The primary interface between the fluid delivery device and the user is via the remote control device.

The device further includes a means of placing an integrated infusion set through the patient's skin, as well as automatically withdrawing a semi-rigid penetrating member. The system of the present invention can avoid the need for a sharpened metal object from ever being exposed both prior to insertion through the skin or after withdrawal of the device from the skin.

Another aspect of the present invention comprises an improved transcutaneous infusion set that utilizes a rigid or semi-rigid penetrating member to place a soft cannula through the skin of the patient. The penetrating member is then removable from the soft cannula to provide better patient comfort by avoiding a sharpened rigid or semi-rigid tip from residing in the patient's subcutaneous tissue.

In one aspect, the penetrating member can be withdrawn from the subcutaneous tissue, but remain encapsulated within the infusion set of the present invention. Retraction means, attached to the penetrating member are detached and removed, leaving the contaminated member with its sharp tip safely contained within the device. The improved infusion set can remain indwelling for a period of time such as three days, with the soft cannula securely located in the patient's subcutaneous tissue, allowing multiple injections during the indwelling period without requiring the repeated piercing of skin with needles.

For applications such as Type I diabetes, patients using syringe injections presently puncture their skin both for the injections and for blood glucose testing. As needle free blood glucose technologies are made available, the need for a needle free subcutaneous access device, such as those described in the present invention will be extremely beneficial.

Another aspect of the present invention comprises an infusion set having a flow restricting element, which can prevent excessive flow rates or pressures to be delivered to the patient. In combination with an elastically compliant section, the system can store medication for short and long periods of time, continuously infusing the liquid medicament by way of the flow restricting element.

These aspects of the invention together with additional features and advantages thereof may best be understood by reference to the following detailed descriptions and examples taken in connection with the accompanying illustrated drawings.

BRIEF DESCRIPTION OF THE DRAWINGS

FIG. 34 is a top plan view, partially in section, of an additional embodiment of a fluid delivery device of the present invention, with a compliant section shown unexpanded; and FIG. 35 is a top plan view, partially in section, of the device of FIG. 34, with the compliant section shown fully expanded and constrained by a restraining element.

DETAILED DESCRIPTION OF THE PREFERRED EMBODIMENTS

Figure 1:
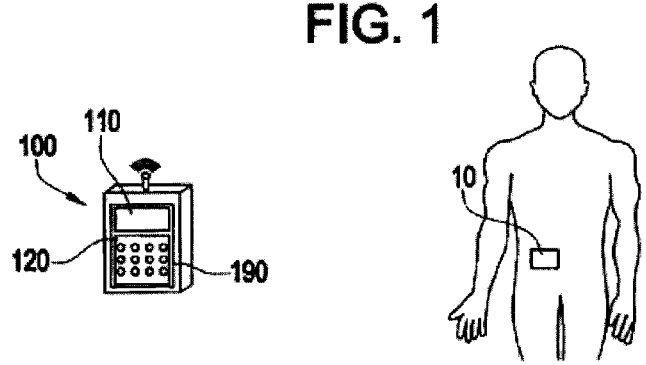
FIG. 1 is a perspective view of a first exemplary embodiment of a fluid delivery device constructed in accordance with the present invention and shown secured on a patient, and a remote control device for use with the fluid delivery device (the remote control device being enlarged with respect to the patient and the fluid delivery device for purposes of illustration)
Figure 2:
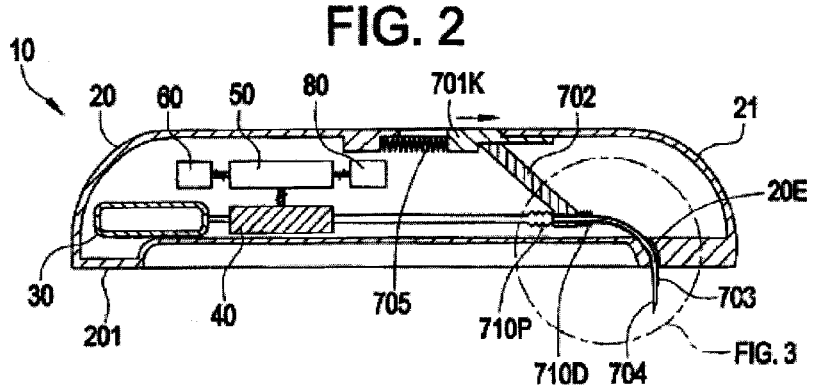
FIG. 2 is a sectional view of the fluid delivery device of FIG. 1, with a slidably movable penetrating member shown deploying a subcutaneous infusion cannula.

Referring first to FIGS. 1 and 2, there is illustrated a fluid delivery device 10 constructed in accordance with the present invention. The types of liquids that can be delivered by the fluid delivery device of the present invention include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device of the present invention might be used to treat include, but are not limited to, diabetes, cardiovascular disease, pain, chronic pain, cancer, AIDS, neurological diseases, Alzheimer's Disease, ALS, Hepatitis, Parkinson's Disease or spasticity.

Referring to FIG. 2, the device 10 generally includes an exit port assembly 70 including a transcutaneous patient access tool, a dispenser 40 for causing fluid from a reservoir 30 to flow to the exit port assembly 70, and a processor or electronic microcontroller (hereinafter referred to as the "local" processor) 50 connected to the dispenser 40.

The local processor 50 is programmed to cause a flow of fluid to the exit port assembly 70 based on flow instructions from a separate, remote control device 100, an example of which is shown in FIG. 1. Referring also to FIG. 2, the fluid delivery device 10 further includes a wireless receiver 60 connected to the local processor 50 for receiving the flow instructions from the separate, remote control device 100 and delivering the flow instructions to the local processor. The device 10 also includes a housing 20 containing the exit port assembly 70, the reservoir 30, the dispenser 40, the local processor 50, and the wireless receiver 60.

As shown, the housing 20 is free of user input components for providing flow instructions to the local processor 50, such as electromechanical switches or buttons on an outer surface 21 of the housing, or interfaces otherwise accessible to a user to adjust the programmed flow rate through the local processor 50. The lack of user input components allows the size, complexity and costs of the device 10 to be substantially reduced so that the device 10 lends itself to being small and disposable in nature.

In order to program, adjust the programming of, or otherwise communicate user inputs to the local processor 50, the fluid delivery device 10 includes the wireless communication element, or receiver 60 for receiving the user inputs from the separate, remote control device 100 of FIG. 1. Signals can be sent via a communication element (not shown) of the remote control device 100, which can include or be connected to an antenna 130, shown in FIG. 1 as being external to the device 100.

Referring to FIGS. 1 and 2, the remote control device 100 has user input components, including an array of electromechanical switches, such as the membrane keypad 120 shown. The control device 100 also includes user output components, including a visual display, such as a liquid crystal display (LCD) 110. Alternatively, the control device can be provided with a touch screen for both user input and output. Although not shown in FIG. 1, the remote control device 100 has its own processor (hereinafter referred to as the "remote" processor) connected to the membrane keypad 120 and the LCD 110. The remote processor receives the user inputs from the membrane keypad 120 and provides "flow" instructions for transmission to the fluid delivery device 10, and provides information to the LCD 110. Since the remote control device 100 also includes a visual display 110, the fluid delivery device 10 can be void of an information screen, further reducing the size, complexity and costs of the device 10.

The communication element 60 of the device 10 preferably receives electronic communication from the remote control device 100 using radio frequency or other wireless communication standards and protocols. In a preferred embodiment, the communication element 60 is a two-way communication element, including a receiver and a transmitter, for allowing the fluid delivery device 10 to send information back to the remote control device 100. In such an embodiment, the remote control device 100 also includes an integral communication element 60 comprising a receiver and a transmitter, for allowing the remote control device 100 to receive the information sent by the fluid delivery device 10.

The local processor 50 of the device 10 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 50 also includes programming, electronic circuitry and memory to properly activate the dispenser 40 at the needed time intervals.

In the exemplary embodiment of FIG. 2, the device 10 includes a power supply 80, such as a battery or capacitor, for supplying power to the local processor 50. The power supply 80 is preferably integrated into the fluid delivery device 10, but can be provided as replaceable, e.g., a replaceable battery.

Although not shown, the device can include sensors or transducers such as a reservoir volume transducer or a reservoir pressure transducer, for transmitting information to the local processor 50 to indicate how and when to activate the dispenser 40, or to indicate other parameters determining flow, pump flowpath prime condition, blockage in flowpath, contact sensors, rotary motion or other motion indicators, as well as conditions such as the reservoir 30 being empty or leaking, or the dispensing of too much or too little fluid from the reservoir, etc.

The volume of the reservoir 30 is chosen to best suit the therapeutic application of the fluid delivery device 10 impacted by such factors as available concentrations of medicinal fluids to be delivered, acceptable times between refills or disposal of the fluid delivery device 10, size constraints and other factors. The reservoir 30 may be prefilled by the device manufacturer or a cooperating drug manufacturer, or may include external filling means, such as a fill port having needle insertion septum or a Luer connector, for example. In addition, the device 10 can be provided with a removable reservoir.

Although not shown, the device 10 can also be provided with an adhesive layer on the outer surface of the housing 20 for securing the device 10 directly to the skin of a patient. The adhesive layer is preferably provided in a continuous ring encircling the exit port assembly 70 in order to provide a protective seal around the penetrated skin. The housing 20 can be made from flexible material, or can be provided with flexible hinged sections that allow the fluid delivery device 10 to flex during patient movement to prevent detachment and aid in patient comfort.

The dispenser 40 is connected in fluid communication with the reservoir 30, as shown in FIG. 2, and controlled by the local processor 50, which includes electronic programming, controls and circuitry to allow sophisticated fluid delivery programming and control of the dispenser 40. When the device 10 is provided with a pressurized reservoir 30 (i.e., fluid maintained within the reservoir at a pressure above atmospheric), the dispenser 40 is configured to act as a metering device, allowing pulses of fluid to pass from the pressurized reservoir 30, through the dispenser 40, to the exit port assembly 70 at atmospheric pressure. When the device 10 is provided with a non-pressurized reservoir 30, the dispenser 40 is configured to create a driving or pumping force on the fluid passing therethrough.

Referring now to FIGS. 2 through 5 and 3a, the present invention provides an improved exit port assembly 70 for use as part of the fluid delivery device 10. The exit port assembly 70 generally includes a flexible transcutaneous cannula 703 extending from the dispenser 40, and a rigid penetrating member 704 positioned within the cannula. The penetrating member 704 is arranged to drive the cannula 703 through a patient's skin and into subcutaneous tissue of the patient, and then be withdrawn to leave the soft cannula 703 in place in the subcutaneous tissue. The improved exit port assembly 70 avoids the disposal of sharp contaminated needles, and patient exposure to sharp points throughout the use of the device 10.

The flexible transcutaneous cannula 703 may be constructed of various materials compatible with the liquid medicines to be delivered such as silicone, polyvinyl chloride, polyethylene or nylon. The penetrating member 704 may be made of a metal such as stainless steel. If flexing of the penetrating member 704 is required, spring steel can be used or elastic metals such as nickel titanium alloy, also referred to as Nitinol.

The exit port assembly also includes penetrating member 704 that has a sharpened distal tip, has a semi rigid construction and can exit transcutaneous infusion cannula 703 to assist in piercing the skin of the patient during placement. The penetrating member may be constructed of spring steel or Nitinol, a nickel titanium alloy with elastic properties. In the construction of fluid delivery device 10 of FIG. 1, the penetrating member 704 would need to curve or otherwise modify its shape during its allowable travel. In a preferred embodiment, the penetrating member has a lumen that allows fluid to flow within its outer walls.

The penetrating member 704 is moved via connecting member 702 to which it is attached. Since the penetrating member 704 resides within the flow path of the device, distal linear expanding and contracting member 710D is connected on one end to the transcutaneous infusion cannula proximal end and on the other end connected to the connecting member 702. A proximal linear expanding and contracting member 710P may be connected on one end to the other side of the connecting member and on its other end to a fluid flow tube connected with dispenser 40. All connections allow flow to pass through while preventing leaks at the connection point.

Figure 3:
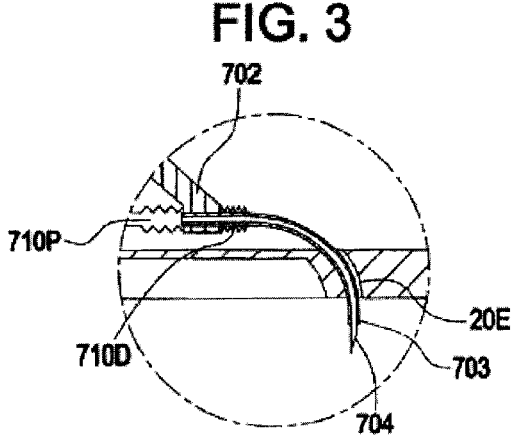
FIG. 3a is a further enlarged sectional view of the portions of the penetrating member and the subcutaneous infusion cannula of FIG. 3.
Figure 3A:
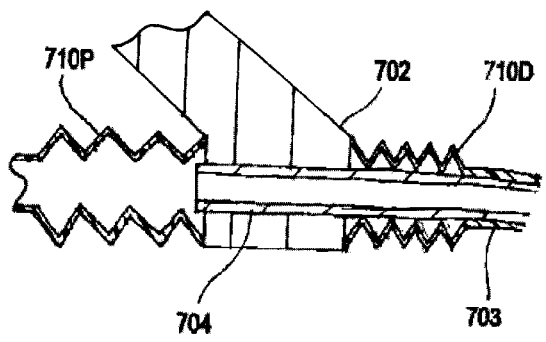

As shown in FIGS. 2 and 3 and 3a, the proximal linear expanding and contracting member 710P and the distal linear expanding and contracting member 710D are tubes constructed to allow one end of the tube to be linearly displaced while the other end is displaced a different distance or no distance at all. A bellows or accordion construction with flexible materials can accomplish this requirement. Material choices for proximal linear expanding and contracting member 710P and distal linear expanding and contracting member 710D may include silicone, polyethylene, polyvinyl chloride, nylon or other materials that are compatible with the fluids being delivered, flexible, and able to be manufactured in the accordion construction.

When constructed and attached as described, and the penetrating member in its retracted position within the confines of housing 20, penetration control knob 701K can be moved forward advancing connecting member 702. As connecting member 702 moves forward, penetrating member 704 moves with it, while distal linear expanding and contracting member 710D contracts, thus penetrating member 704 slidably moves within the lumen of the transcutaneous infusion cannula 703 exiting the tip. To maintain sealed fluid connections of the system, as connecting member 702 is moved forward by penetration control knob 701K, proximal linear expanding and contracting member 710P stretches. Alternatively in the absence of proximal linear expanding and contracting member 710P, the tubing connecting to the connecting member 702 may be flexible and of sufficient length to permit the range of motions of the assembly.

FIGS. 2 and 3 show penetration control knob 701K moved forward, penetration control spring 705 elongated, proximal linear expanding and contracting member 710P expanded, distal linear expanding and contracting member 710D contracted, and penetrating member 704 extended beyond the tip of transcutaneous infusion cannula 703.

If penetrating member 704 is already extended, as is shown in FIGS. 2 and 3, penetration control knob 701K can be moved back, correspondingly moving back connecting member 702 which is connected to penetrating member 704. Flexible transcutaneous cannula 703 can remain in place in the subcutaneous tissue of the patient since the motion can be absorbed by the contraction of distal linear expanding and contracting element 710D.

In a preferred embodiment of the present invention, penetration control knob 701K is attached to penetration control spring 705 which biases penetration control knob 701K to automatically retract penetrating member 704 whenever penetrating member 704 has been extended. In use, the patient would move the penetration control knob 701K to extend penetrating member 704, place the fluid delivery device 10 onto their skin, such as in the abdominal area, piercing the skin with the penetrating member 704 and transcutaneous infusion cannula 703, and further secure the fluid delivery device 10 to their body with medical adhesive tape. In a preferred embodiment, the fluid delivery device 10 may include housing adhesive layer 201, such as an adhesive ring around the boundary of the device, to attach to a patient's skin. Once the patient has let go of the penetration control knob 701K, the penetration member 704 automatically retracts due to the bias of penetration control spring 705, leaving the soft infusion cannula, transcutaneous infusion cannula 703 in place in the subcutaneous tissue of the patient.

As shown in FIGS. 2 through 5, the outside diameter of the penetration member 704 approximates the inner diameter of the flow tubes in which it resides such as transcutaneous infusion cannula 703 and the distal linear expanding and contracting member 710D. Since the penetrating member 704 remains within the flow path of the device after retraction, fluid flows through the lumen of penetrating member 704 to reach the distal tip of transcutaneous infusion cannula 703. In an alternative embodiment, the penetrating member 704 can have an outside diameter less than the flow tubes in which it resides, allowing fluid to flow around the penetrating member 704 and obviating the need for an internal lumen within penetrating member 704.

Figure 4:
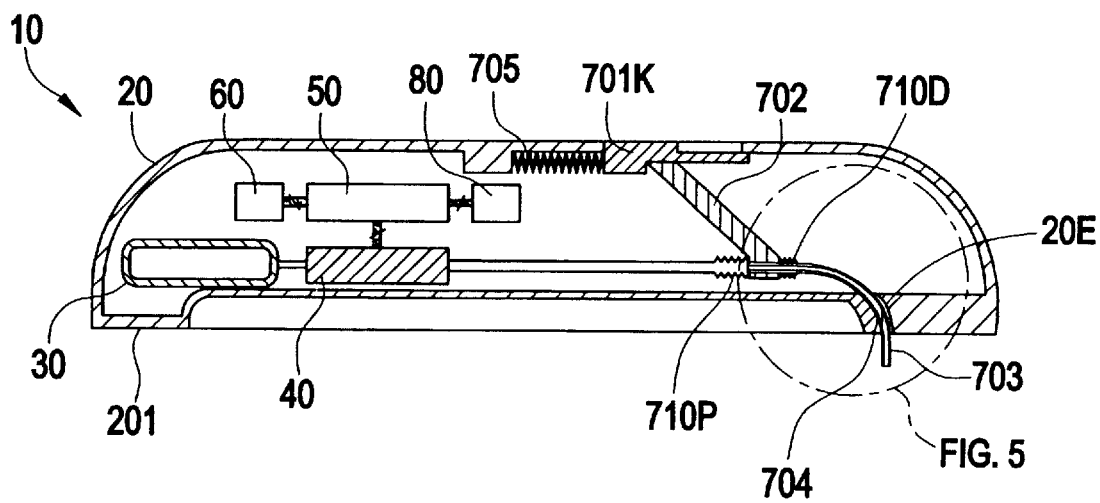
FIG. 4 is a sectional view of the fluid delivery device of FIG. 1, with the slidably movable penetrating member shown retracted into a lumen of the subcutaneous infusion cannula.
Figure 5:
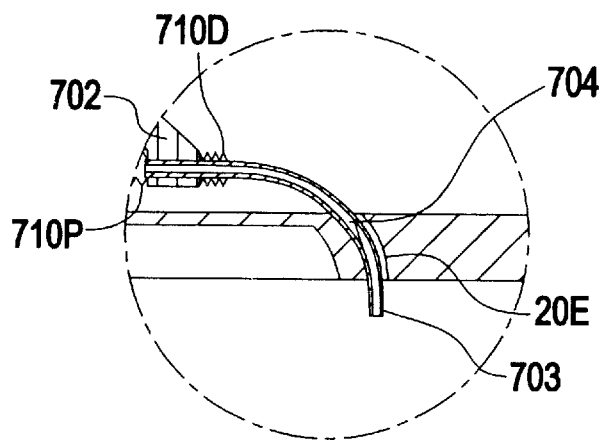
FIG. 5 is an enlarged sectional view of the portions of the penetrating member and the subcutaneous infusion cannula of the fluid delivery device contained in circle 5 of FIG. 4.

FIGS. 4 and 5 show the fluid delivery device 10 of FIG. 1 after the penetration control knob 701K has been released and the penetration control spring 705 is in its rest state with no potential energy stored. In addition, the proximal linear expanding and contracting member 710P is shown contracted, the distal linear expanding and contracting member 710D is extended, and the penetrating member 704 is retracted within the housing 20 and the lumen of transcutaneous infusion cannula 703.

Figure 6:
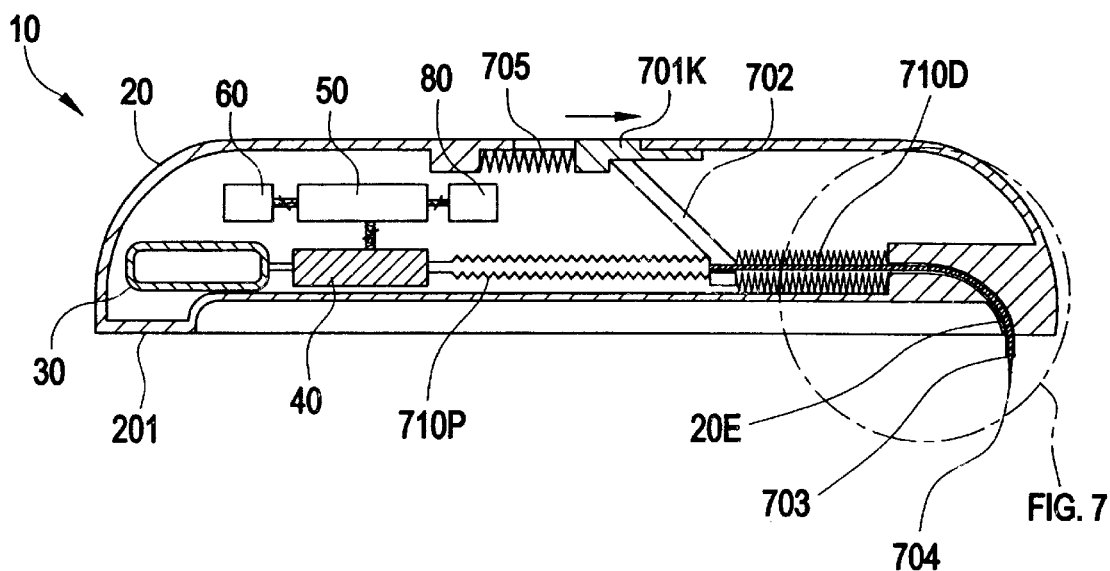
FIG. 6 is a sectional view of another embodiment of a fluid delivery device of the present invention, with a slidably movable penetrating member shown exiting a subcutaneous infusion cannula.

Referring to FIG. 6, another embodiment of the fluid delivery device 10 of the present invention is shown, having a solid penetrating member 704 with an outside diameter less than an inside diameter of distal linear expanding and contracting member 710D, such that fluid can flow around the penetrating member 704.

Figure 7:
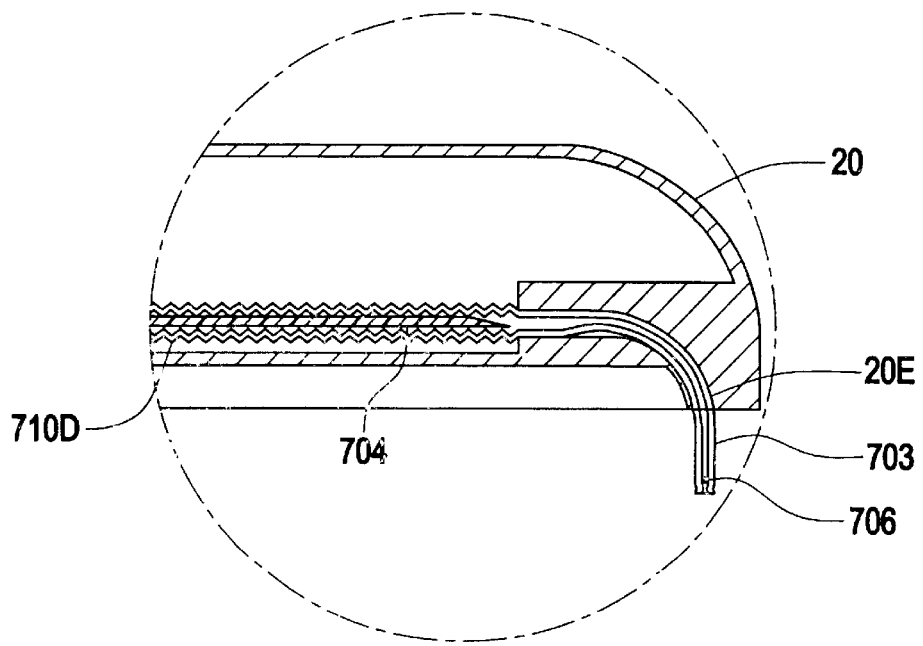
FIG. 7 is an enlarged sectional view of the portions of the penetrating member and the subcutaneous infusion cannula of the fluid delivery device contained in circle 7 of FIG. 7.

As shown best in FIG. 7, the flexible transcutaneous infusion cannula 703, which exits the housing 20 of fluid delivery device 10 by way of housing exit 20E, includes one or more side holes 706 so that fluid can exit the distal tip of the cannula as well as exit holes proximal to the tip. Optionally, the distal tip may be sealed forcing all of the fluid to exit through the one or more side holes 706.

Figure 8:
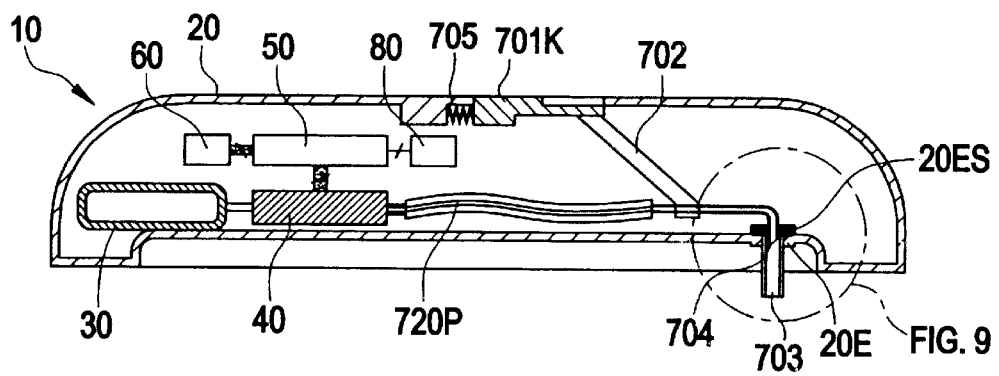
FIG. 8 is a sectional view of an additional embodiment of a fluid delivery device of the present invention, with a penetrating member shown located within a subcutaneous infusion cannula prior to advancement.
Figure 9:
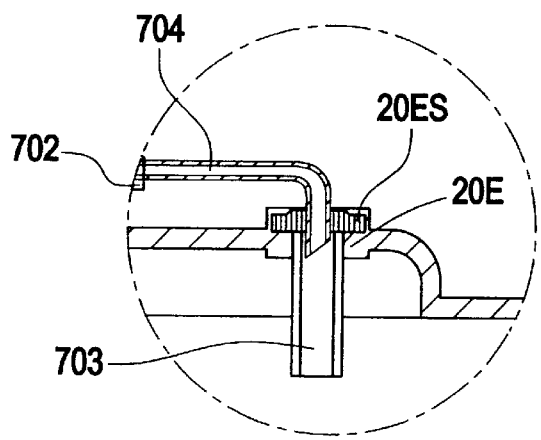
FIG. 9 is an enlarged sectional view of the portions of the penetrating member and the subcutaneous infusion cannula of the fluid delivery device contained in circle 9 of FIG. 8.
Figure 10:
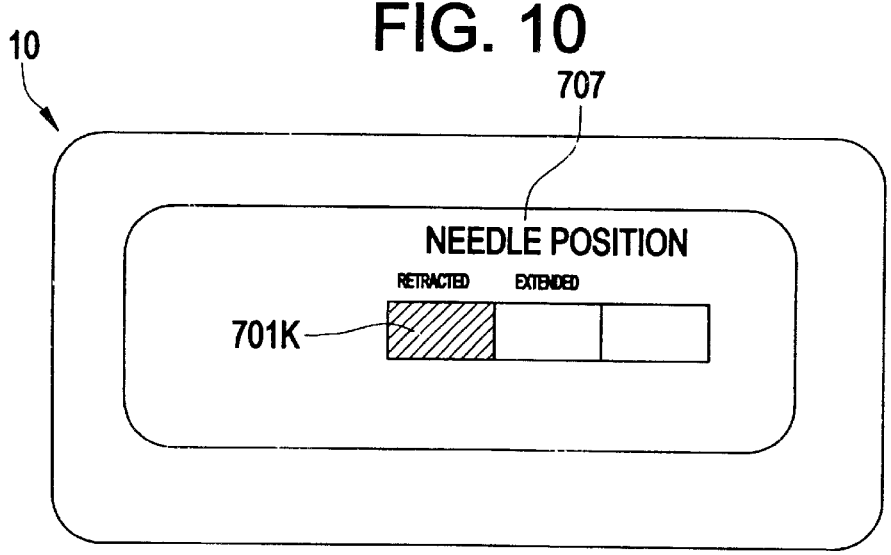
FIG. 10 is a top plan view of the fluid delivery device of FIG. 9, showing a needle position indicator of the device.

FIGS. 8 through 10, depict another embodiment of a fluid delivery device 10 of the present invention, having a movable, hollow penetrating member 704 connected to a flexible tube 720P that is slidably connected to an infusion cannula 703 through a housing exit seal 20ES. FIG. 8 depicts the fluid delivery device 10 with the penetrating member 704 in a retracted state.

The penetration control knob 701K is connected to the connecting member 702 wherein a force applied to penetration control knob 701K with sufficient force to overcome the bias of penetration control spring 705, would cause the connecting member 702 to move forward, advancing penetration member 704 further through housing exit seal 20ES causing the distal tip of penetrating member 704 to exit flexible transcutaneous cannula 703. When in the advanced state, the penetrating member 704 and the flexible transcutaneous cannula 703 can penetrate the skin of the patient. Then the penetration control knob 701K can be released to allow the bias from the penetration control spring 705 to cause retraction of the connecting member 702 and the penetrating member 704 so that the tip of penetrating member 704 is pulled back within the lumen of flexible transcutaneous cannula 703 and into the housing exit port 20E.

The proximal end of the penetrating member 704 is in a sealed fluid connection to proximal fluid transport tube 720P. Proximal fluid transport tube 720P is of sufficient length and flexible construction to support full travel of penetrating member 704. Proximal fluid transport tube 720P is constructed of flexible materials that are compatible with the chosen fluids to be delivered. Examples of these materials include silicone, polyethylene, polyvinyl choride, nylon and other materials. Alternatively, proximal fluid transport tube 720P could include a bellows or accordion construction, such as the proximal linear expanding and contracting member 710P shown in FIG. 1.

FIG. 9 shows the penetration member 704 retracted into the housing exit port 20E but remaining through the housing exit seal 20ES and within the lumen of the flexible transcutaneous cannula 703. FIG. 10 shows a top view of the fluid delivery device 10, which includes a needle position indicator 707 that provides a visual indication to a user as to the location of the penetrating member 704. The top of penetration control knob 701K correlates to text or other visual indicators included in needle position indicator 707 that indicate the position of penetrating member 704. FIG. 10 correlates with FIGS. 8 and 9 in that the penetration control knob 701K is in a retracted state, with penetration member 704 retracted, and that the needle position indicator 707 indicates a retracted state.

Figure 11:
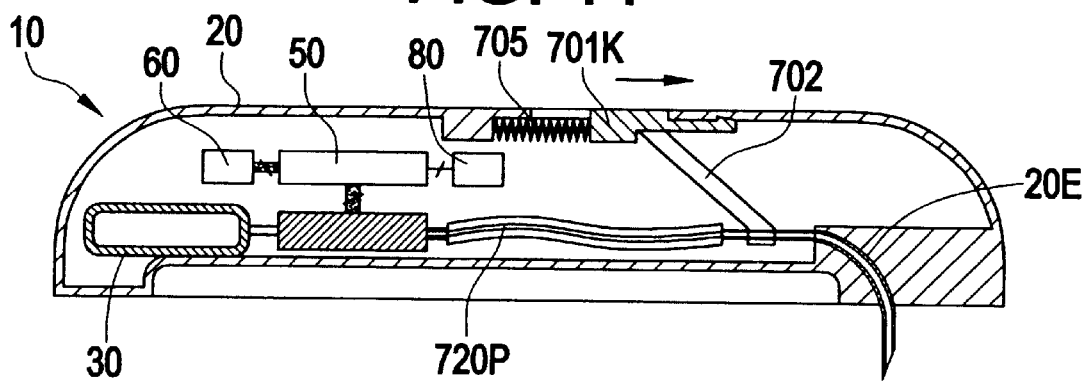
FIG. 11 is a sectional view of the fluid delivery device of FIG. 8, with the penetrating member shown located distal to the tip of the subcutaneous infusion cannula.

FIG. 11 shows another embodiment of the fluid delivery device 10 of the present invention including an advanceable penetrating member 704 connected to a flexible tube 720P that is in fluid communication with the dispenser 40. The fluid delivery device 10 is shown with the penetrating member 704 in its fully advanced state. When in the advanced state, the penetrating member 704 is adapted to penetrate the skin of a patient. In addition, after advancement, the penetration control knob 701K is locked in place via a latch of the knob 701K engaging a cut out in the housing 20 to secure the penetration member 704 in an advanced position.

In the embodiment shown in FIG. 11, the penetrating member 704 is required to flex during advancement to make an approximate right angle turn through exit 20E in housing 20. The penetrating member is, therefore, made of material sufficient to support penetration of the patient's skin, yet flexible enough to bend during advancement and retraction. Examples of suitable materials include spring steel, and nickel titanium alloy, known as Nitinol. Alternatively, a design wherein the penetrating member 704 travels solely in a direction perpendicular to the patient's skin, i.e. up and down, and wherein the proximal fluid transport tube 720P bends can be provided. In such a design, the penetrating member 704 can be a rigid construction and made from a non-flexible material such as standard or hypodermic grade stainless steel. In either construction, the penetrating member 704 is hollow to support fluid flow, and can include a sharpened tip to assist in penetrating the skin of the patient.

Figure 12:
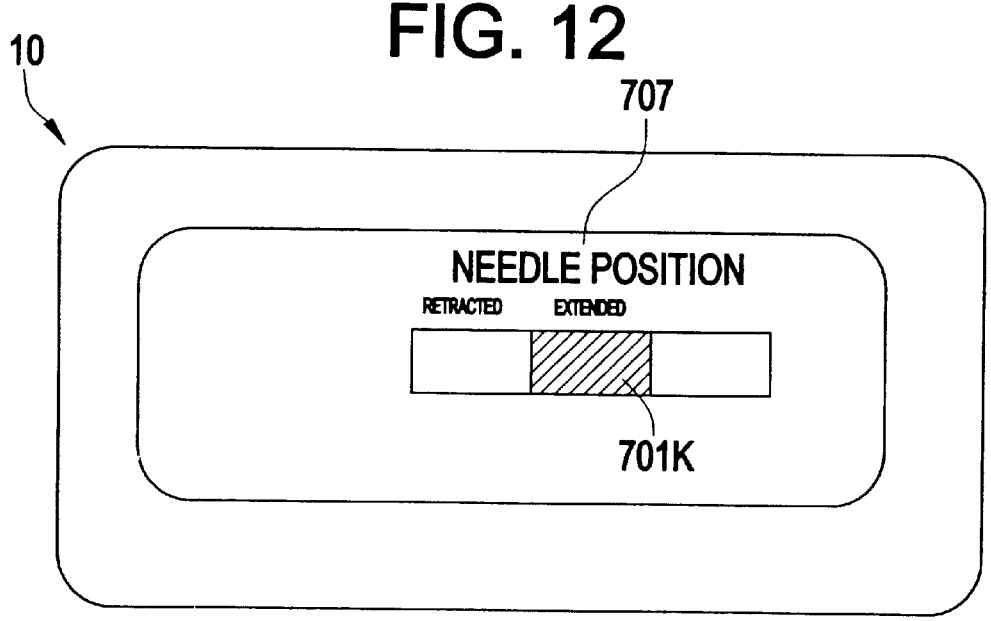
FIG. 12 is a top plan view of the fluid delivery device of FIG. 11, showing the needle position indicator.

As shown in FIG. 12, the embodiment of FIG. 11 includes a needle position indicator 707 that provides visual feedback to a user as to the location of the penetrating member 704. The top of penetration control knob 701K correlates to text or other visual indicators included in needle position indicator 707 that indicate the position of penetrating member 704. FIG. 12 correlates with FIG. 11 in that the penetration control knob 701K is in its extended and locked state, with penetration member 704 advanced as is indicated via needle position indicator 707.

FIGS. 13 through 17 show another preferred embodiment of the fluid delivery device 10 of the present invention, shown attached on a patient's skin 210 and wherein an exit port assembly 70 includes a penetration control button 701B extending through a button clearance hole 740 of the housing 20 for advancing and retracting a transcutaneous penetrating member 704. The penetration control button 740 is movable in opposing directions perpendicular to the skin 210 and is fixedly attached to a connecting member 702. The connecting member 702 has a fluid pathway connected between proximal fluid transport tube 720P, that in turn is connected to the dispenser 40, and to distal linear expanding and contracting member 710D. All connections are made to allow flow between components without leaks. The distal linear expanding and contracting member 710D is fluidly connected to a distal fluid transport tube 720D that is in turn fluidly connected to a flexible transcutaneous cannula 703. Residing within the distal linear expanding and contracting member 710D and the flexible transcutaneous cannula 703, and fixedly attached to the connecting member 702 is the penetrating member 704.

Figure 13:
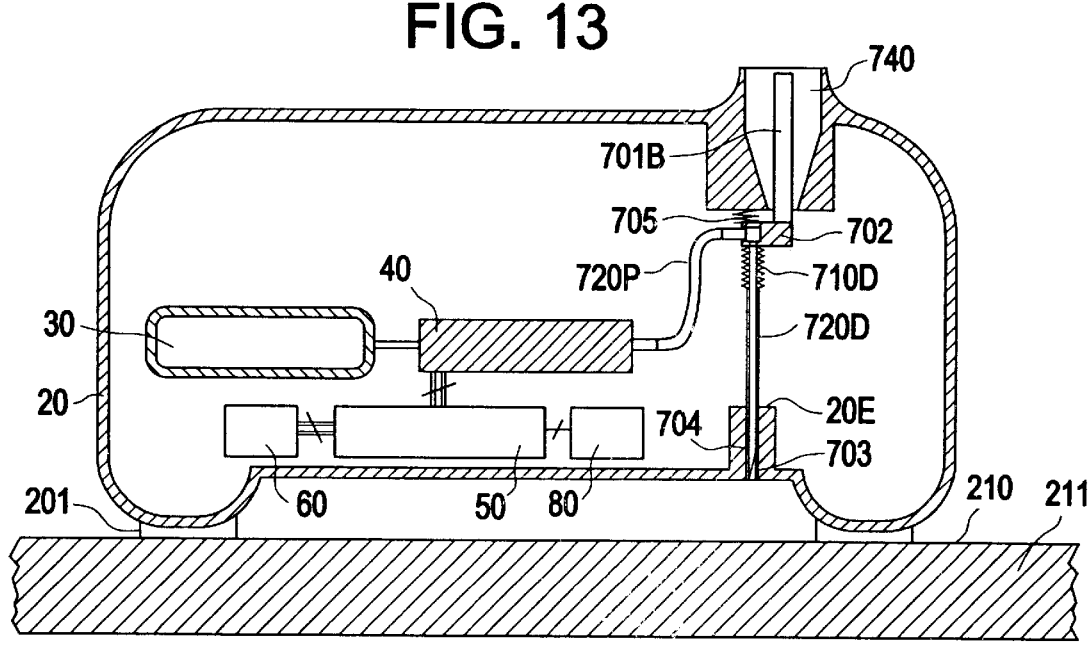
FIGS. 13 through 17 are sectional views of a further embodiment of a fluid delivery device of the present invention positioned on a patient's skin, illustrating a penetrating member prior, during and after deployment.
Figure 14:
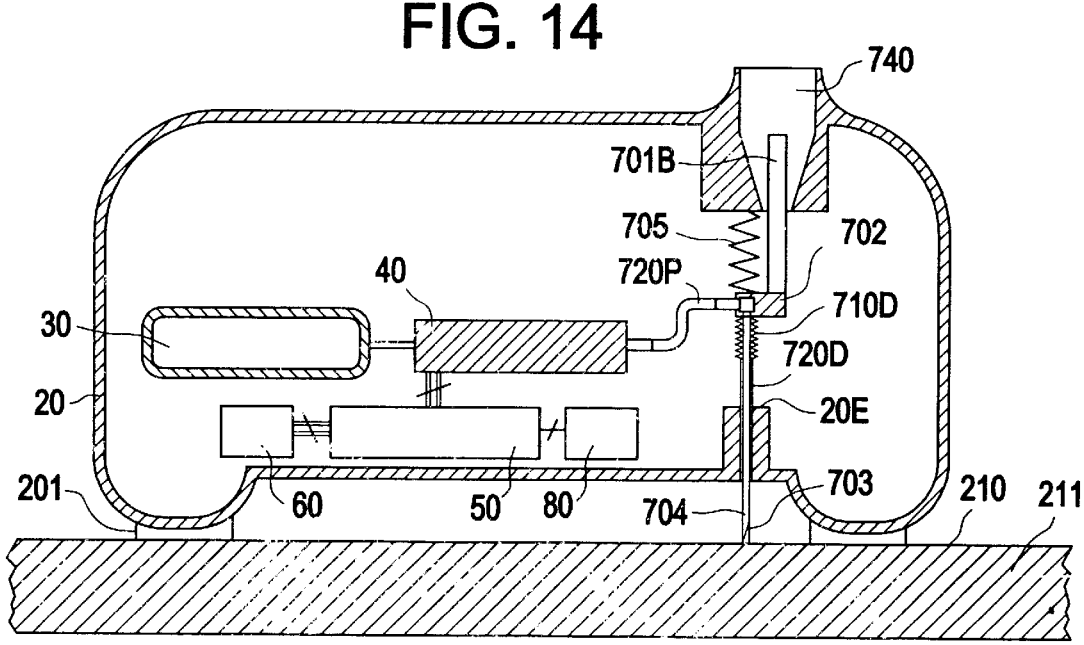
Figure 15:
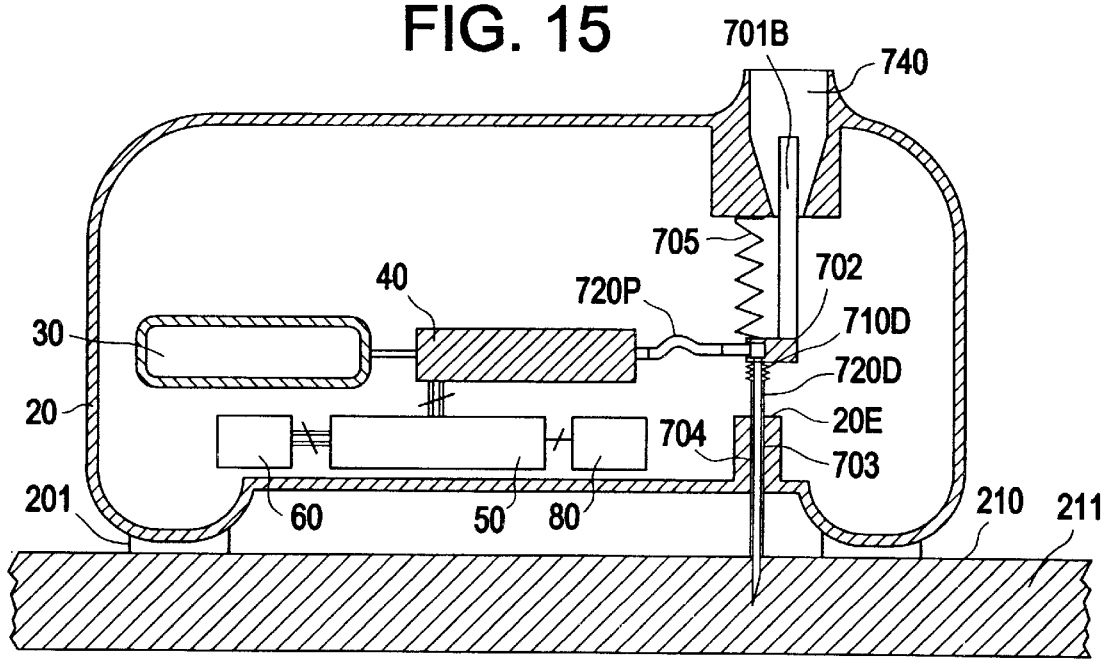

In FIG. 13, the penetration control button 701B is shown in an initial, non-depressed position, such that the penetration control spring 705 is fully contracted, the flexible transcutaneous cannula 703 is withdrawn into the housing exit port 20E, and the penetrating member 704 is withdrawn into the flexible transcutaneous cannula 703. FIG. 13 also shows that the device 10 has been attached to the skin of the patient 210 via adhesive 201. FIG. 14 shows the penetration control button 701B being into the button clearance hole 740, such as with a patient's finger (not shown), and causing the proximal fluid transport tube 720P and the distal fluid transport tube 720D to move toward the skin 210, the penetration control spring 705 to expand, and the penetrating member 704 and the cannula 703 to advance to the surface of the skin 210. FIG. 12 shows further depression of the penetration control button 701B causing the proximal fluid transport tube 720P and the distal linear expanding and contracting member 710D to move further towards the skin, the penetration control spring 705 to further expanded, and the penetrating member 704 to penetrate the skin 210 and enter subcutaneous tissue 211 of the patient. The elongated, tubular housing exit port 20E supports the flexible transcutaneous cannula 703 and the penetrating member 704 and provides additional column strength to assist in penetrating the surface of patient's skin 210.

Figure 16:
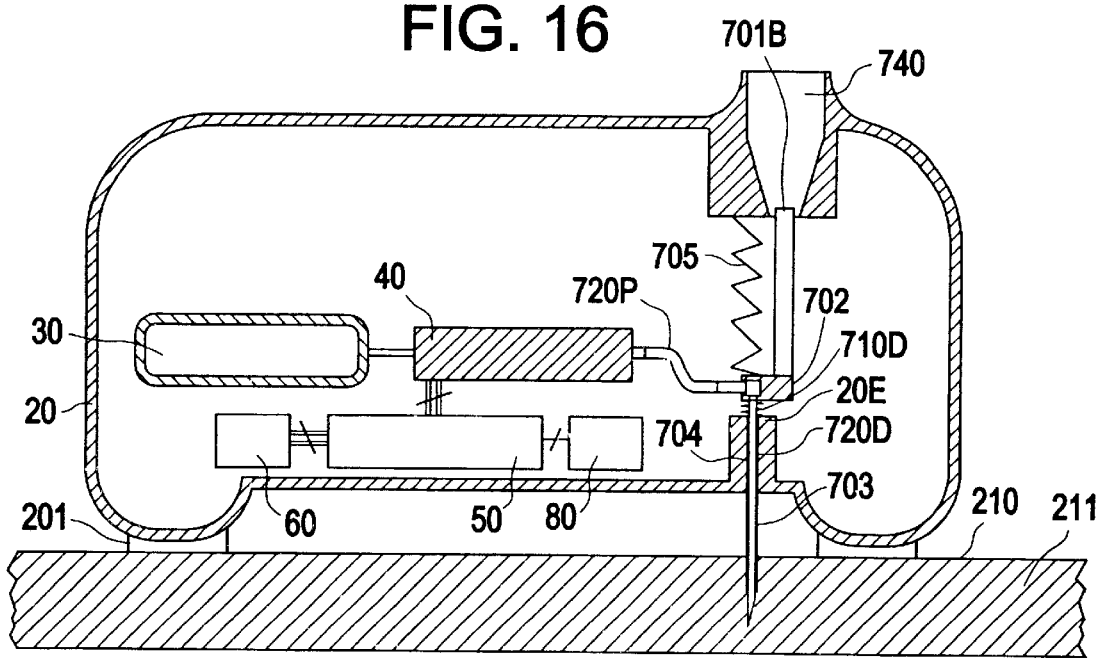
Figure 17:
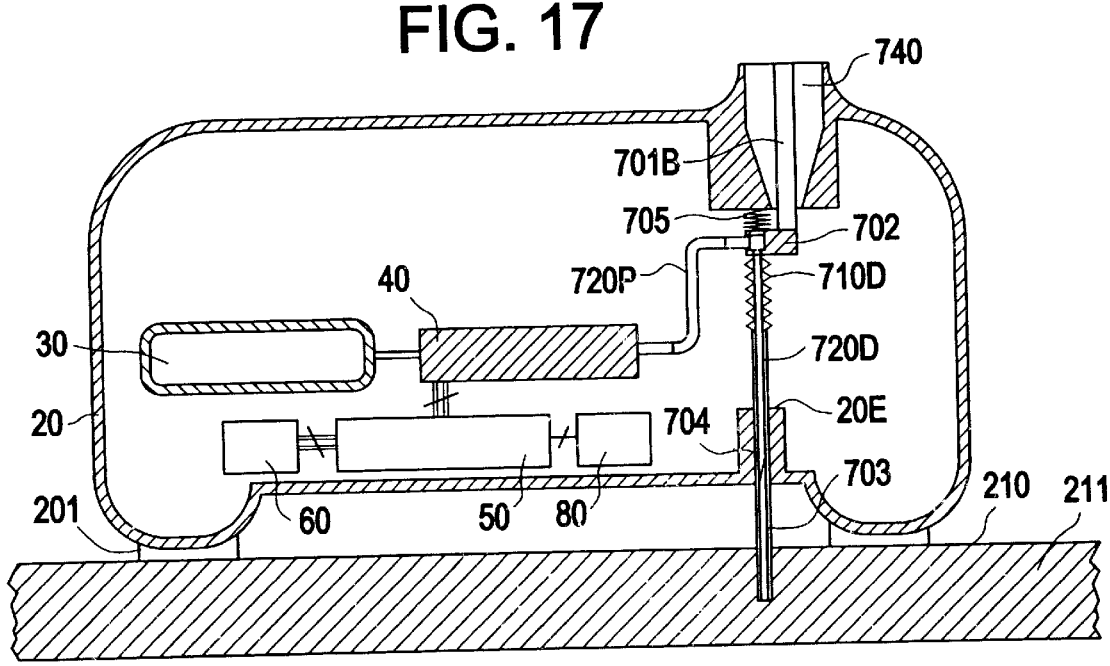

FIG. 16 shows furthermost depression of the penetration control button 701B into the button clearance hole 740, causing full expansion of the penetration control spring 705, further advancement of the proximal fluid transport tube 720P, the distal linear expanding and contracting member 710D in contact with the housing exit port 20E, the flexible transcutaneous cannula 703 advanced through the skin 210 and into subcutaneous tissue 211 of the patient, and the penetrating member 704 further advanced through the skin 210 and the subcutaneous tissue 211. FIG. 17 shows the penetration control button 701B after being released, such that the penetration control spring 705 has been allowed to contract and return the button in a direction away from the skin 210 and back up into the button clearance hole 740, causing the penetrating member 704 to be retracted back into the flexible transcutaneous cannula 703 and within the housing exit port 20E. As shown, however, the flexible transcutaneous cannula 703 remains through the skin 210 and in the subcutaneous tissue 211 of the patient.

In order to hold the flexible transcutaneous cannula 703 within the subcutaneous tissue 211 and prevent the flexible transcutaneous cannula 703 from being retracted into the housing exit port 20E as the penetrating member 704 is slidably retracted, the housing exit port 20E can be provided with a rough inner surface for frictionally engaging the flexible transcutaneous cannula 703. Alternatively, the surface of the housing exit port 20E can be provided with angled frictional engaging members, not shown, to allow smooth advancement of the flexible transcutaneous cannula 703 towards the skin 210 and prevent movement of the flexible transcutaneous cannula 703 away from the skin 210.

All connections described allow fluid to pass from component to component without leaks. The distal linear expanded and contracting member 710D allows relative quantity and direction of motion between the penetrating member 704 and the flexible transcutaneous cannula to differ, enabling the preferred embodiment of the invention. In addition, a second spring (not shown) can be utilized to provide automatic insertion force bias, i.e., bias towards the skin. Speed of skin penetration can be an important factor in pain reduction, and utilizing a second spring, activated by pushing or turning the penetration control button 701B, and deactivated when the penetration member 704 reaches its maximum downward travel, can be beneficial.

Figure 18:
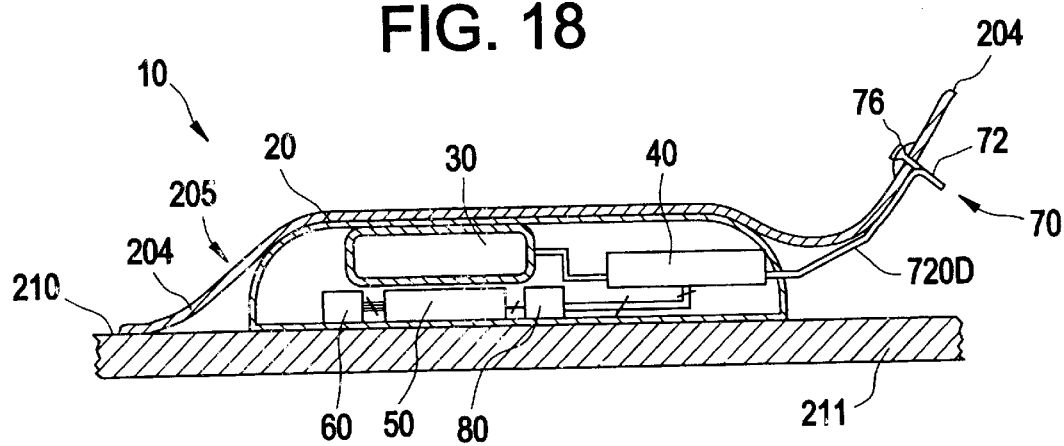
FIG. 18 is a sectional view of still another embodiment of a fluid delivery device of the present invention, shown positioned on a patient's skin.

FIG. 18 shows another embodiment of a fluid delivery device 10 constructed in accordance with the present invention. The device 10 of FIG. 18 includes an adhesive membrane 205 covering the housing 20 for attaching the device 10 to a patient's skin 210, and having projections 204 projecting out from the housing 20. An exit port assembly 70 is integrated into one of the adhesive axial projections 204 and is connected to the dispenser 40 through distal fluid transport tube 720D. The exit port assembly 70 includes a skin penetrating cannula 72, such as a hypodermic needle or a flexible cannula, as described above, in fluid communication with the distal fluid transport tube 720D and a cannula access septum 76. The cannula access septum 76 is adapted to allow a needle (not shown) to penetrate through the septum while the septum maintains a seal, such that the needle can inject liquids through the skin penetrating cannula 72 into the patient. When the needle is removed, the cannula access septum 76 seals the needle puncture tract. The septum 76 is maintained in a compressed state, such as with a compressing housing (not shown), to assist in sealing and the septum is made of an appropriate material, such as a silicon elastomer. The distal fluid transport tube 720D may include a one-way check valve (not shown) to prevent fluid entering the cannula access septum 76 from flowing backwards into the dispenser 40.

Figure 19:
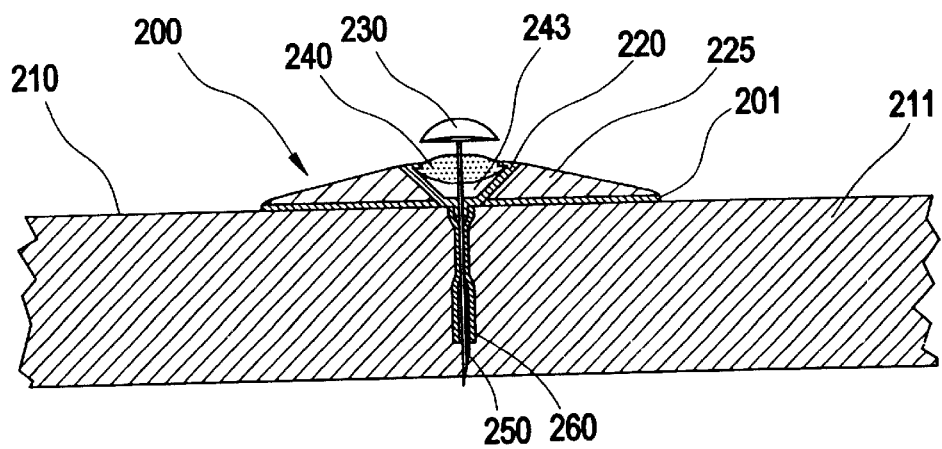
FIG. 19 is a sectional view of another embodiment of a fluid delivery device of the present invention, shown positioned on a patient's skin.

FIG. 19 depicts a transcutaneous infusion button 200 of the present invention, including a housing 220 that surrounds an inlet valve 240. The housing 220 may be constructed of a plastic such as acetyl or polysulfone or a metal such as stainless steel or titanium. For low cost production, injection molded plastics are preferable. The inlet valve 240 can be a mechanical valve including a Luer connection for attachment to a standard syringe, not shown, or alternatively a needle penetrable septum made from a material such as silicone, as shown.

Defined by the housing 220 below the inlet valve 240 is a reservoir 243. Surrounding the housing 220 is a flexible section 225 that includes a bottom surface and an adhesive layer 201 on the bottom surface. Attached to the housing 220 is a subcutaneous infusion cannula 260 that is in fluid communication with the inlet valve 240. Prior to first use, a transcutaneous penetrator 250 is contained within the lumen of the subcutaneous infusion cannula 260. In the embodiment shown, the penetrator 250 is hollow. Attached to the proximal end of the transcutaneous penetrator 250 is a detachable retractor 230 that passes through the inlet valve 240. Placement of the device involves penetration of the surface of patient's skin 210 by the transcutaneous penetrator 250 until the housing adhesive layer 201 is firmly in contact with the surface of patient's skin 210 and subcutaneous infusion cannula 260 resides in the subcutaneous tissue 211.

Figure 20:
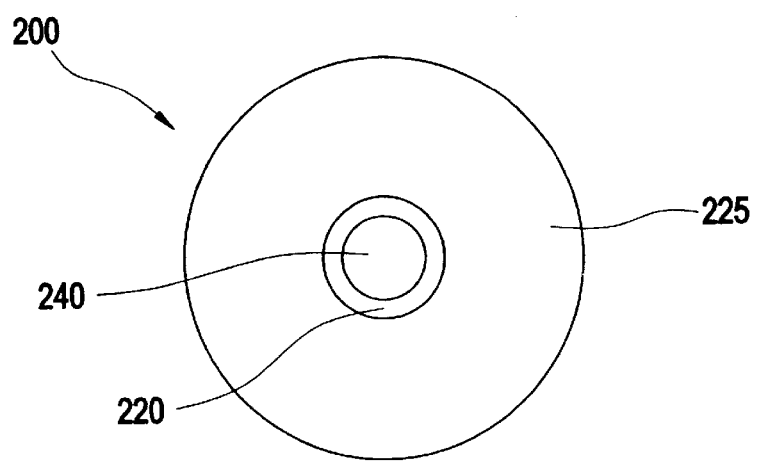
FIG. 20 is a top plan view of the device of FIG. 19.

FIG. 20 shown a top view of the transcutaneous infusion button 200 showing the flexible section 225 surrounding the housing 220 and the inlet valve 240. The flexible section 225 is made of a flexible material such as silicon elastomer, and allows relative motion of the patient's skin. The adhesive 201 can be standard epidermal adhesives such as those used in bandaids, or adhesives such as those employed by Tyco Valley Lab in their electrosurgery pads.

Figure 21:
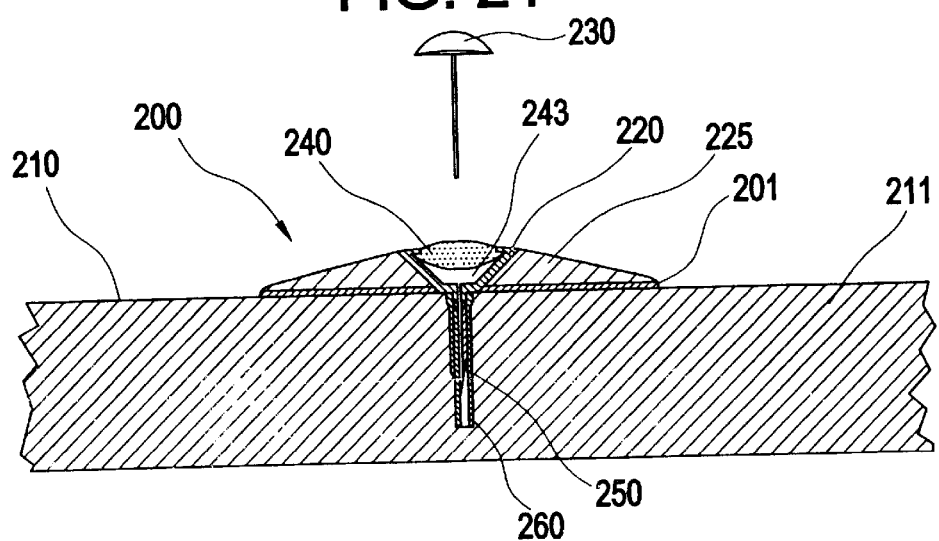
FIG. 21 is a sectional view of the fluid delivery device of FIG. 19, with a penetrating member shown pulled back and a retraction means removed.

In FIG. 21 the detachable retractor 230 has been pulled out of the transcutaneous penetrator 250 within the lumen of the subcutaneous infusion cannula 260, and removed from the inlet valve 240. With the transcutaneous infusion button 200 in place, and the retractor 230 removed, access can be made with a syringe and a needle, through the inlet valve 240 to deliver fluids through the hollow transcutaneous penetrator 250 and into the subcutaneous tissue 211 via the subcutaneous infusion cannula 260.

The outside diameter of the transcutaneous penetrator 250 is larger than the inside diameter of the subcutaneous cannula 260. The subcutaneous cannula 260 is designed and constructed of materials that allow the subcutaneous cannula 260 to radially expand in the area surrounding the transcutaneous penetrator 250 and allow the transcutaneous penetrator 250 to slidably move within the subcutaneous cannula 260 when retracted by the detachable retractor 230 without causing the detachable retractor 230 to prematurely detach from the transcutaneous penetrator 250. A lubricant, such as silicone emulsion provided by Nusil Corporation or Dow Corporation can be used to lubricate the internal surface of subcutaneous infusion cannula 260 to support ease of movement of the transcutaneous penetrator 250. The smaller inner diameter of the subcutaneous infusion cannula 260 may be more clinically acceptable and the larger outer diameter of the transcutaneous penetrator may aid in transcutaneous puncturing by the device. Alternatively, the transcutaneous penetrator 250 may have an outside diameter similar to the inside diameter of the subcutaneous cannula 260 or slightly smaller.

Figure 22:
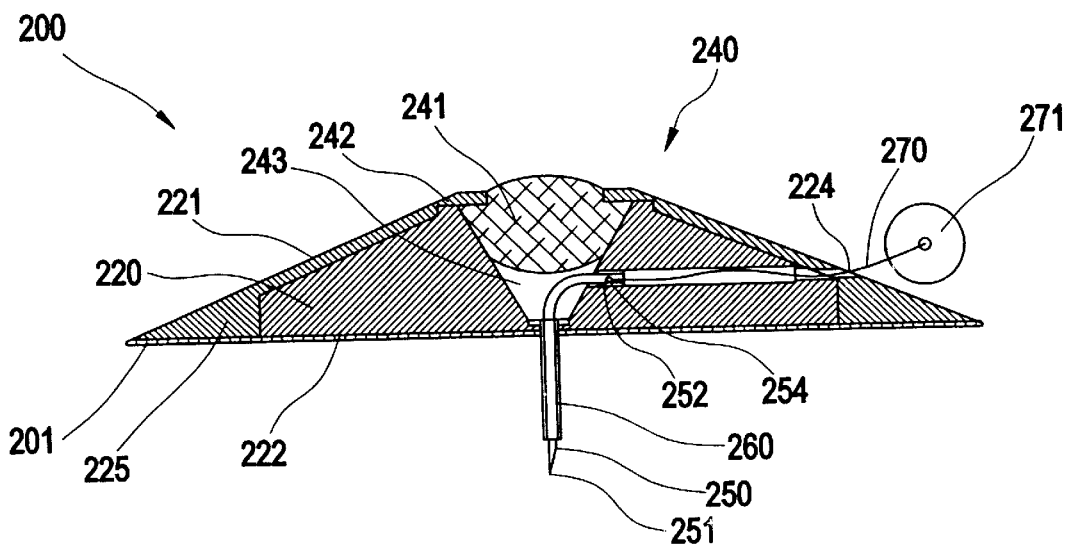
FIG. 22 a sectional view of an additional embodiment of a fluid delivery device of the present invention, showing a penetrating member and an infusion cannula deployed and a retractor connected to the device.

FIG. 22 is another preferred embodiment of the present invention including a transcutaneous infusion button 200 that includes a penetrating member 250 and a detachable retractor 270 for retracting the penetrator to a position within the device. The infusion button 200 also includes a housing 220, preferably constructed of injection molded plastic such as acetyl to reduce weight and cost, and a top surface 221 and a flexible section 225 surrounding the housing and constructed of a soft, flexible material such as silicone elastomer to allow flexing and provide comfort to a patient wearing the button 200. A bottom surface 222 of the button 200 includes an adhesive layer 201 for attaching the button to a patients skin.

The button also includes an inlet valve 240 having an inlet septum 241 surrounded and radially compressed by a septum ring 242. The inlet septum 241 is received in a reservoir 243 of the button 200. A subcutaneous infusion cannula 260 is in fluid communication with the inlet valve 240 and exits the bottom portion of the housing 220. Prior to placement into the patient, a tip 251 of the transcutaneous penetrator 250 exits the tip of the subcutaneous infusion cannula 260. On the proximal end of transcutaneous penetrator 250 is penetrator sealing element 252 used to create a fluid seal when the penetrator is retracted. Also located on the proximal end of the transcutaneous penetrator 250 is attachment hole 254 to which retractor 270 is affixed at its distal end. The retractor 270 enters the transcutaneous infusion button 200 via detachment exit port 224. At the proximal end of retractor 270 is detachment grasp 271, which extends out of the housing 220 and can be pulled by a user after transcutaneous penetration by the device 200, to withdraw the penetrator tip 251 of the transcutaneous penetrator 250 in the lumen of the subcutaneous infusion cannula 260.

Figure 23:
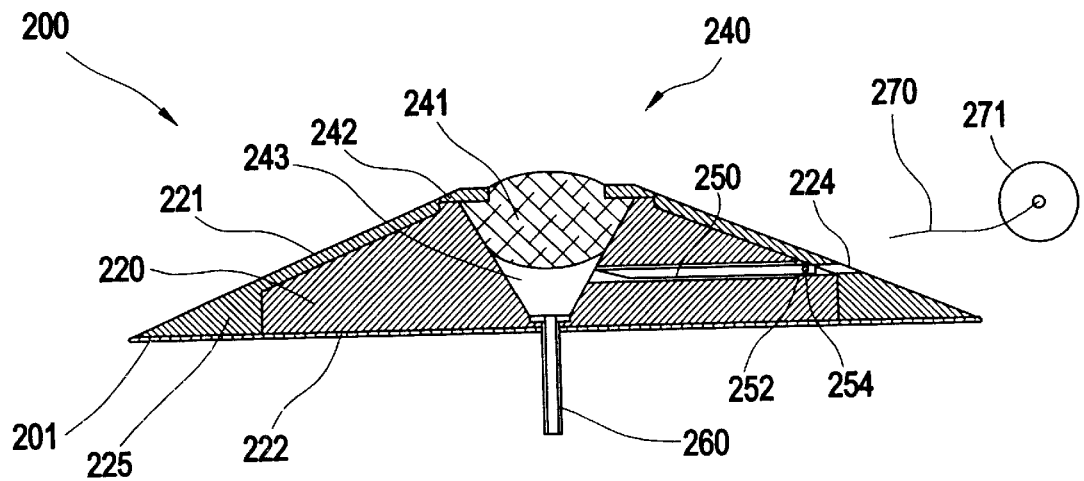
FIG. 23 is a sectional view of the device of FIG. 22, showing the penetrating member withdrawn into the device, the infusion cannula deployed, and the retractor detached.

As shown in FIG. 23, the transcutaneous penetrator 250 exits the transcutaneous infusion button 200 through a separate, detachment exit port 224, whose exit path is parallel to the patient's skin requiring a right angle or near right angle exit trajectory. The transcutaneous penetrator 250 is, therefore, constructed of an elastic material, preferable a metal such as nickel, titanium alloy or a spring steel. As shown in FIG. 23, the retractor 270 can fully retract the transcutaneous penetrator 250 into the exit port 224 within the housing, avoiding presence of the penetrator in the subcutaneous infusion cannula 260 or any part of the fluid path. The transcutaneous penetrator 250 can be a solid tube or a hollow tube.

FIG. 23 depicts the transcutaneous penetrator 250 fully pulled back with the penetrator sealing element 252 creating a fluid seal to the infusion button housing 220 thus preventing leaks during infusions. As also shown, the retractor 270 becomes detached from the transcutaneous penetrator 250 and can be discarded. The retractor 270 does not include any sharp edges, and is not contaminated by body fluids, making for easy, safe, sanitary disposal of the detached retractor.

Figure 24:
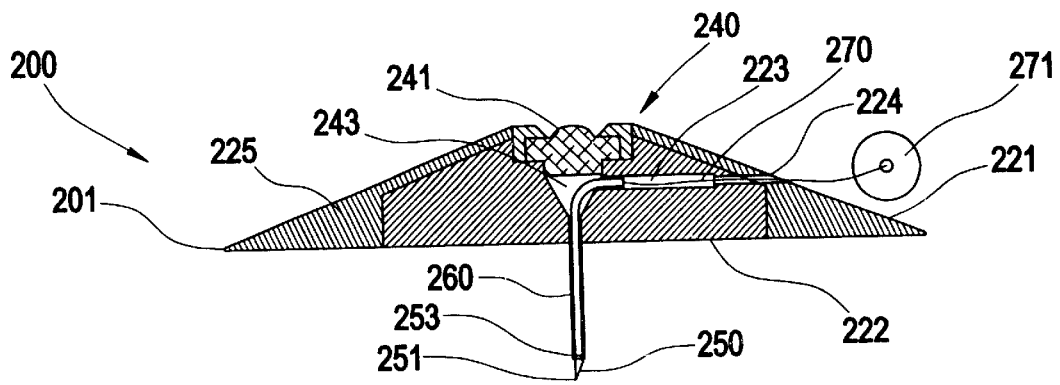
FIG. 24 a sectional view of a further embodiment of a fluid delivery device of the present invention, showing a penetrating member and an infusion cannula deployed and a retractor connected to the device.
Figure 25:
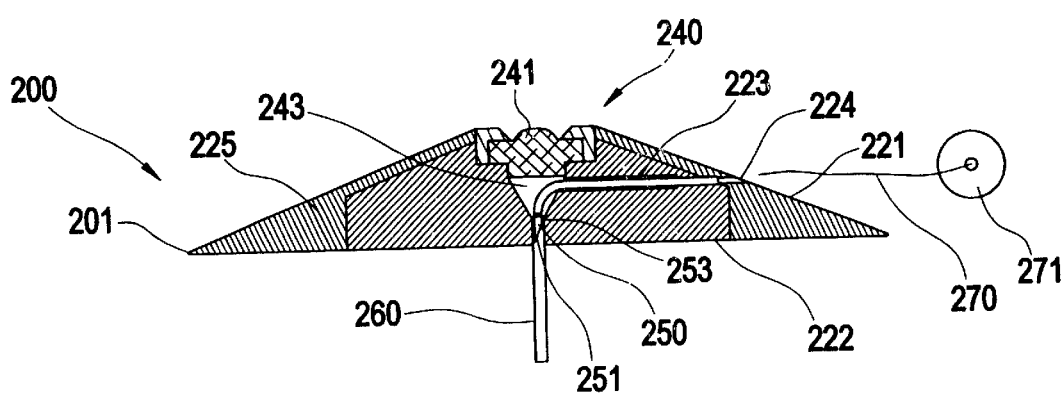
FIG. 25 is a sectional view of the device of FIG. 22, showing the penetrating member withdrawn into the device, the infusion cannula deployed, and the retractor detached.

FIG. 24 shows an additional embodiment of a transcutaneous infusion button 200, wherein the distal tip 251 of the penetrator 250 is hollow and includes at least one lateral opening 253. The penetrator 250 is adapted such that, when the penetrator 250 is pulled back by the retractor 270, as shown in FIG. 25, the penetrator 250 still resides within the infusion cannula 260. Flow through the button 200 to the patient is accomplished by passing through the lateral hole 253 and hollow tip 251 of the penetrator 250.

Figure 26:
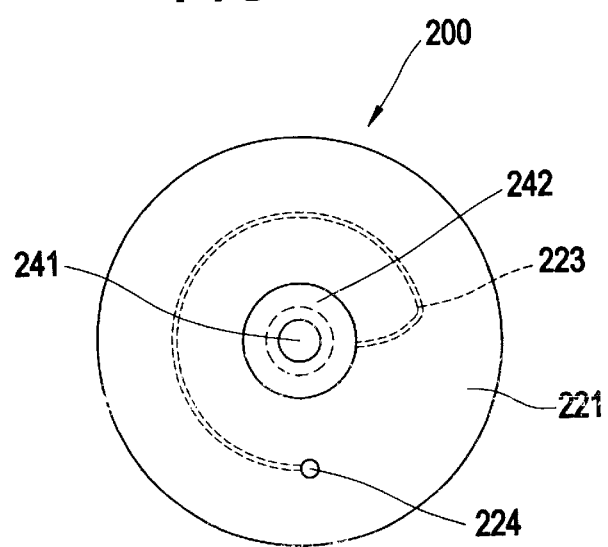
FIG. 26 is a top plan view of yet another embodiment of a fluid delivery device of the present invention.

FIG. 26 shows a top plan view of another embodiment of a transcutaneous infusion button 200 having a detachment exit path 223 within the housing 220 and exiting at detachment exit port 224. As shown, the detachment exit path 223 takes a circuitous route allowing the detachment member, not shown, or transcutaneous penetrator, not shown, to have a linear length that is longer than a lateral dimension of the button 200, e.g., the radius of the embodiment of the button 200 illustrated in FIG. 26. The circuitous path of the detachment exit path 223 allows a penetrator to be longer and still be retracted fully from the fluid path of the infusion button 200.

Figure 27:
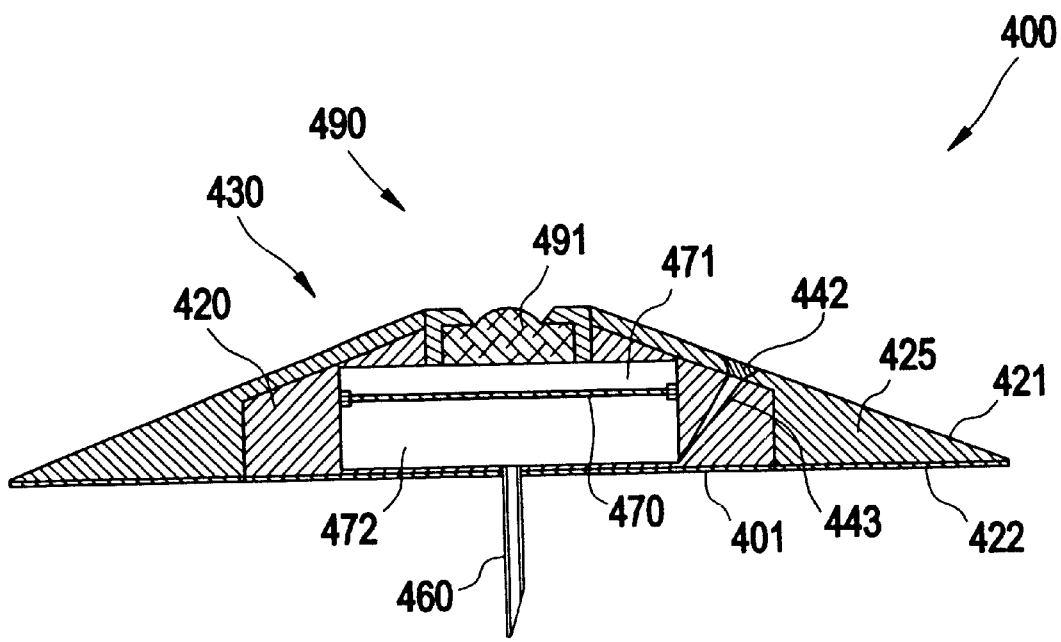
FIG. 27 is a sectional view of a further embodiment of a fluid delivery device of the present invention.

FIG. 27 depicts another preferred embodiment of the present invention including button pump assembly 400 that allows a non-infusate to be delivered into a separate chamber thus causing the intended infusate to be delivered into a patient. Similar in construction to the previously described buttons 200, the button pump assembly 400 includes an inlet valve 490 having an inlet septum 491 surrounded by a pump housing 420, which is in turn surrounded and covered by a flexible section 425 which includes housing top surface 421. The bottom surface 422 of the device includes an adhesive layer 401.

Defined by the button pump housing 420 is a reservoir 430, which is preferably cylindrical. Exiting the bottom of the reservoir 430 is a subcutaneous infusion cannula 460, which may be a soft cannula or semi-rigid or rigid structure, such as a needle. Dividing the reservoir 430 into a fluid displacement section 471 and a medication section 472 is a movable plunger 470. When fluid is added to the displacement reservoir section 471 by way of the inlet valve 490, the reservoir plunger 470 moves towards the infusion cannula 460 and expels an equivalent amount of fluid from the medication reservoir section 472 through the cannula.

The medication reservoir section 472 can be prefilled prior to distribution to patients and caregivers, or can include a medication reservoir entry tube 443 as shown in FIG. 27. The medication reservoir entry tube 443 extends from a medication reservoir entry valve 442, such as a needle penetrable septum, and the bottom of the medication reservoir section 472. The device can be filled with a specific amount of medication, and then, as any fluid, such as water or saline, is administered into the displacement reservoir section 471 by way of inlet valve 490, the reservoir plunger 470 will move downward, forcing an equivalent amount of therapeutic fluid out of the device exiting via subcutaneous infusion cannula 460. The advantage of the button 400 is simplification of the drug delivery process, including avoiding the need for the patient to separately carry with them a supply of medication. A simple syringe, using tap water can be used to give the proper amount of therapeutic medication, since the tap water will never actually enter the patient due to a fluid seal created by the reservoir plunger 470.

It should be appreciated that all of the elements shown in the buttons 200 of previous figures can be included in the button pump assembly 400 of FIG. 27. The inlet valve may allow access with a needle or mechanical connection such as standard Luer connectors. The device may include a flow restrictor to prevent over pressurization. Additionally, a compliant section may be included, or the subcutaneous infusion cannula 460 may be compliant and include a flow restrictor within its lumen, such that fluid is accumulated and delivered over a prolonged period of time to the patient, as is described hereinabove. A penetrating member, with exit path and potentially retractor can be included to aid in transcutaneous placement of subcutaneous infusion cannula 460. Subcutaneous infusion cannula 460 may be constructed of stainless steel, Nitinol, or compliant materials such as silicone, polyvinyl chloride, polyethylene, or other materials.

Figure 28:
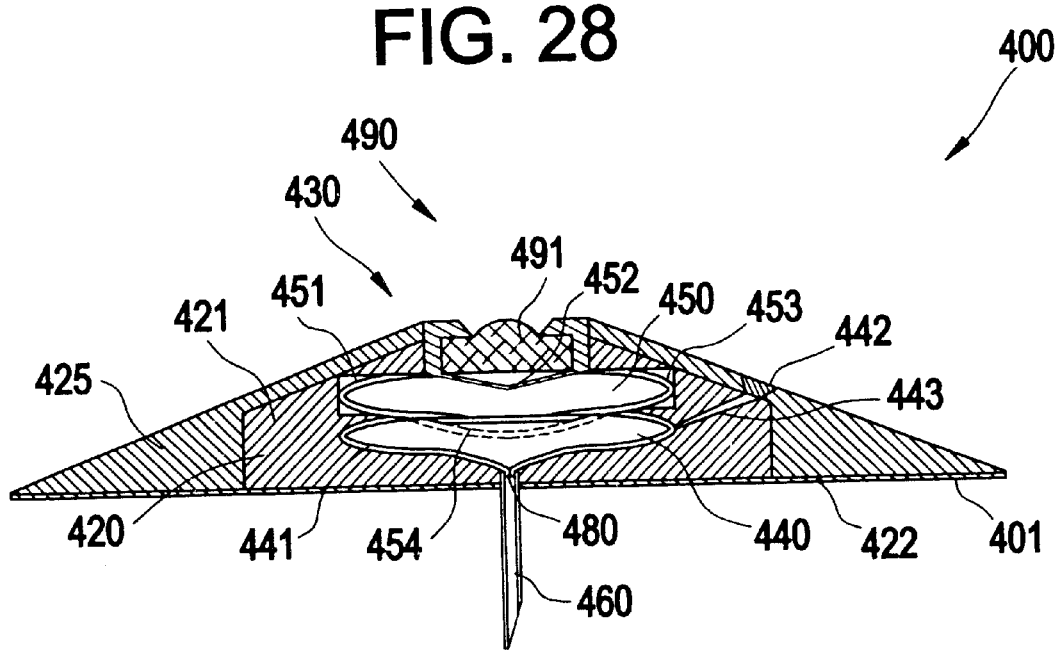
FIG. 28 is a sectional view of another embodiment of a fluid delivery device of the present invention.

FIG. 28 shows another button pump assembly 400 similar to the device of FIG. 27, but including two separate, flexible, sealed reservoirs 440, 450 in mechanical communication with one another such that any force exerted on or from one reservoir is correspondingly exerted on the other reservoir. A volume of non-infusate can be delivered into the non-infusate reservoir 450 to cause an equivalent volume of therapeutic infusate to be delivered to the patient from the infusate reservoir 440. Similar in construction to the device of FIG. 27, the button pump assembly 400 includes an inlet valve 490 having a septum 491.

Contained in the reservoir 430 is a compliant displacement reservoir membrane 451 that defines the non-infusate reservoir 450, which is in fluid communication with the inlet valve 490 by way of a check valve 452. A space 453 for expansion is provided between the reservoir membrane 451 and the housing 420 so that the membrane 451 can elastically expand and pressurize the non-infusate fluid contained therein. Venting holes may be included to allow unimpeded expansion of the displacement reservoir membrane 451.

Also contained within reservoir chamber 430 of the housing 420 is compliant membrane 441 defining the infusate reservoir 440, which is connected to the subcutaneous infusion cannula 460. Located between the infusate reservoir 440 and the subcutaneous infusion cannula 460 is a flow valve 480, which may be a simple one-way check valve or a more complicated flow restricting assembly.

Figure 29:
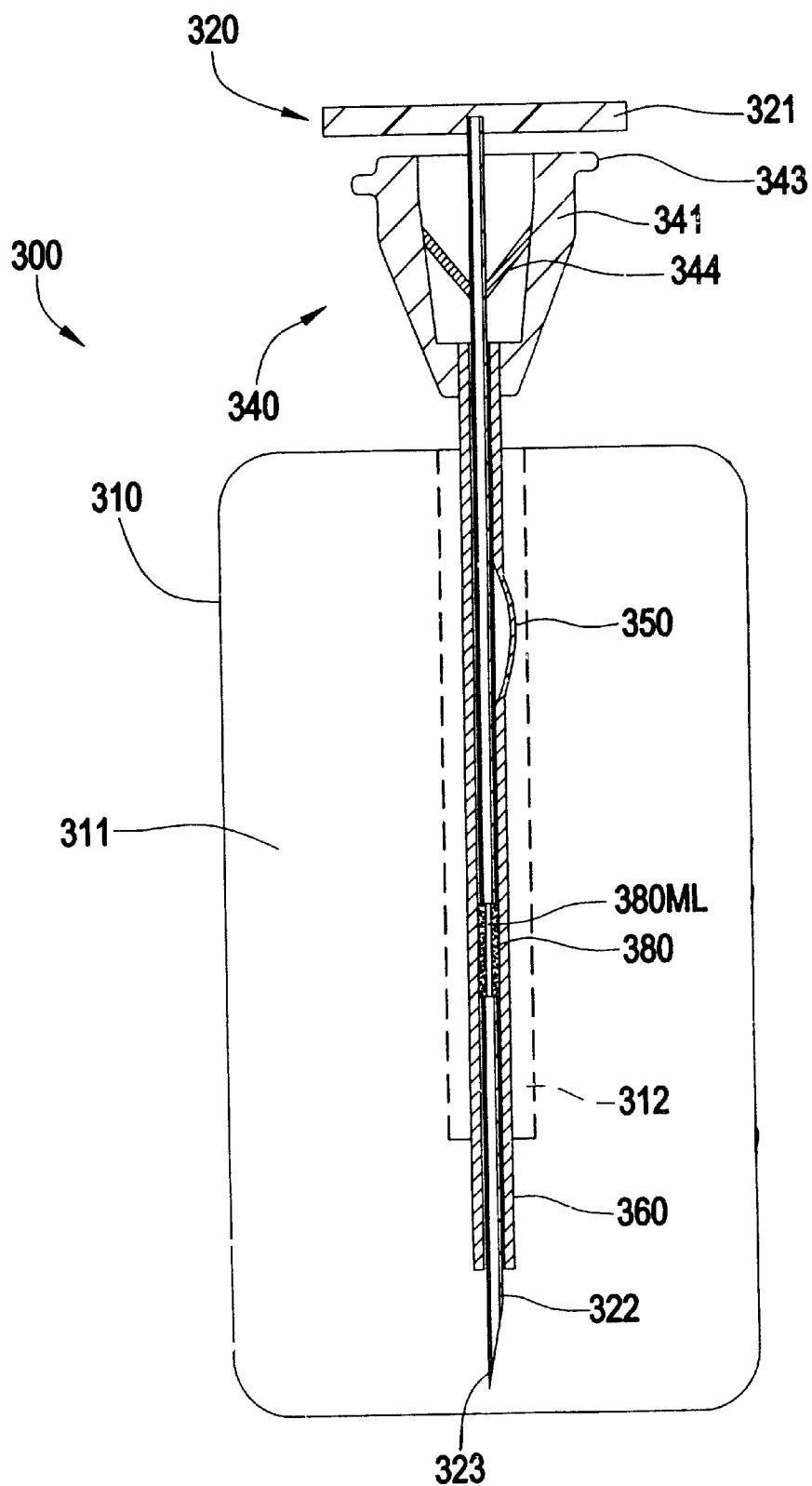
FIG. 29 is a top plan view, partially in section, of an additional embodiment of a fluid delivery device of the present invention.

FIG. 29 depicts another preferred embodiment of a fluid delivery device 300 of the present invention, wherein a flow restricting element 380 is included in a fluid path of the device. The device 300 includes an injector hub 340 for attachment to a standard Luer connector, such as those included on standard syringes. The injector hub 340 consists of injector housing 341 and injector hub male threads 343 for mating with female threads on standard female Luers. The injector hub 340 includes a check valve 344 that controls flow into a subcutaneous cannula 360, a portion of which is designed to reside in the subcutaneous tissue of a mammalian patient. If the injector hub 340 included a penetrable resealing septum to provide needle access instead of being adapted for connecting to a Luer connector, the check valve 344 would not be required.

Within the fluid path of the fluid delivery device 300 and proximal to the distal tip of the subcutaneous infusion cannula 360 is a flow restrictor 380. The flow restrictor 380 includes a micro lumen such as a restrictor micro lumen 380ML that restricts flow per Poissons's equation, but can alternatively be provided with a more complex flow restricting structure such as osmotic membranes or other semipermeable barriers. The micro lumen 380ML can be collinear with the infusion cannula 360 or can take a circuitous route involving many turns to achieve sufficient length to achieve the flow restricting requirements. The subcutaneous infusion cannula 360 may be attached to a skin patch 310 including on one side a suitable adhesive 311. A patch cannula connecting zone 312 is included bonding the subcutaneous infusion cannula 360 to the skin patch 310 and allowing the distal portion of subcutaneous infusion cannula 360 to remain unattached for flexing away from the skin patch 310 into and through the skin of a patient.

One function of the flow restrictor 380 is to limit the pressure that can be delivered to the patient at the distal dip of the cannula 360. Such over-pressure conditions can lead to serious adverse events such as dislodgment, trauma, vessel damage, etc. By limiting the flow, the flow restrictor 380 causes a significant pressure drop such that no significant pressure level can be reached and delivered into the patient.

Proximal to the flow restrictor 380 may be a compliant section such as an expandable accumulator 350. The expandable accumulator 350 is an elastically compliant assembly, with near zero volume in its ambient or unexpanded state. The expandable accumulator 350 is designed such that when fluid is injected into the device via the injection port 340, fluid passes though check valve 344 and the flow restrictor 380 provides sufficient back pressure to cause the expandable accumulator 350 to expand with the injected fluid. The expanded accumulator 350, in turn, causes the fluid therein to be at an elevated pressure. Over time, fluid passes through the flow restrictor 380 and exits the device 300 via the distal tip of subcutaneous infusion cannula 360.

Based on the pressures created by the expandable accumulator 350 and the flow restricting properties of the flow restrictor 380, the length of time and flow profile of the resulting infusion can be determined. Lower pressures and larger restrictions can result in infusion over longer periods of time, which can be beneficial as compared with standard syringe injections in certain therapies such as treatment of diabetes with insulin. In an alternative embodiment, the subcutaneous cannula 360 may be made of an elastically compliant material, such that the section of the subcutaneous cannula that is located proximal to the flow restricting element 380 functions as the accumulator 350, thereby avoiding the need for additional components or materials to function as the accumulator 350.

As also shown in FIG. 29, the fluid delivery device 300 also includes a transcutaneous penetrating member 320 extending through the injector hub 340, the subcutaneous cannula 360, and exiting the distal tip of the cannula 360. The penetrating member aids in placing the tip of the subcutaneous cannula 360 through the skin and into the subcutaneous tissue of the patient. The penetrating member 320 may pass through the flow restrictor 380 or may alternatively pass alongside it. If the subcutaneous cannula 360 is made of an elastically compliant material such as silicone, the subcutaneous infusion cannula can create a fluid seal around the penetrating member 320 while it resides between the outside diameter of the flow restrictor 380 and the inside diameter of subcutaneous cannula 360, and then when the penetrating member 320 is removed, the subcutaneous cannula 360 creates a fluid seal around flow restrictor 380 for continued use.

The penetrating member 320 includes a penetrator hub 321 to allow a patient to remove the penetrator member 320 from the fluid delivery device 300 after placement of the cannula 360 into the subcutaneous tissue of the patient. The penetrator member 320 also includes a penetrator cannula 322 and a sharpened distal tip 323 to aid in penetrating through the patient's skin into the subcutaneous tissue. The penetrator cannula 322 may be made of a rigid or semi-rigid metal such as stainless steel or other materials mentioned hereinabove.

Figure 30:
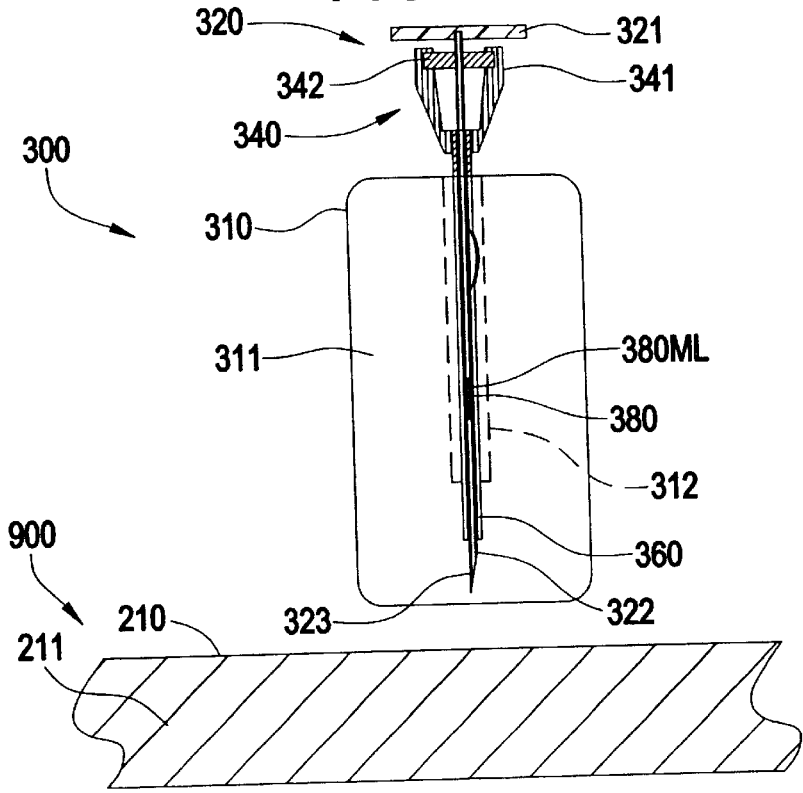
FIG. 30 is a sectional view of the device of FIG. 29, shown just prior to insertion of a penetrating member of the device into a patient's skin.
Figure 31:
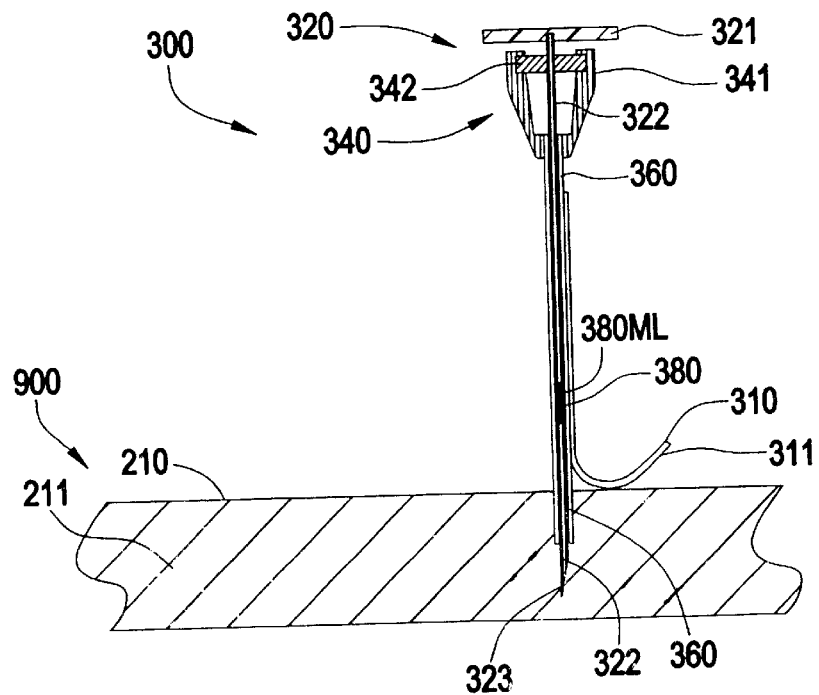
FIG. 31 is a sectional view of the device of FIG. 29, rotated ninety degrees from the view of FIG. 30, showing the penetrating member and a subcutaneous infusion cannula inserted through the skin and into subcutaneous tissue of the patient.

FIGS. 30 and 31 show a fluid delivery device penetrating the skin 200 of a patient 900 and being fixedly attached to the skin. The fluid delivery device of FIG. 30 is similar to the device of FIG. 29, but includes a needle septum 342 instead of a Luer connector and a check valve, in the injector hub 340.

FIG. 30 shows the fluid delivery device 300 with the penetrating member 320 in place about to puncture the surface of the skin 210 and enter subcutaneous tissue 211. As shown, the device is held relatively perpendicular to the surface of patient's skin 210. A preferred method is to quickly jab the penetrator point 323 through the surface of patient's skin 210, which in turn causes the distal portion of the subcutaneous cannula 360, potentially up to the beginning of patch cannula connecting zone 312, into the patient 900 along with the distal portion of penetrator cannula 322, as shown in FIG. 31.

Figure 32:
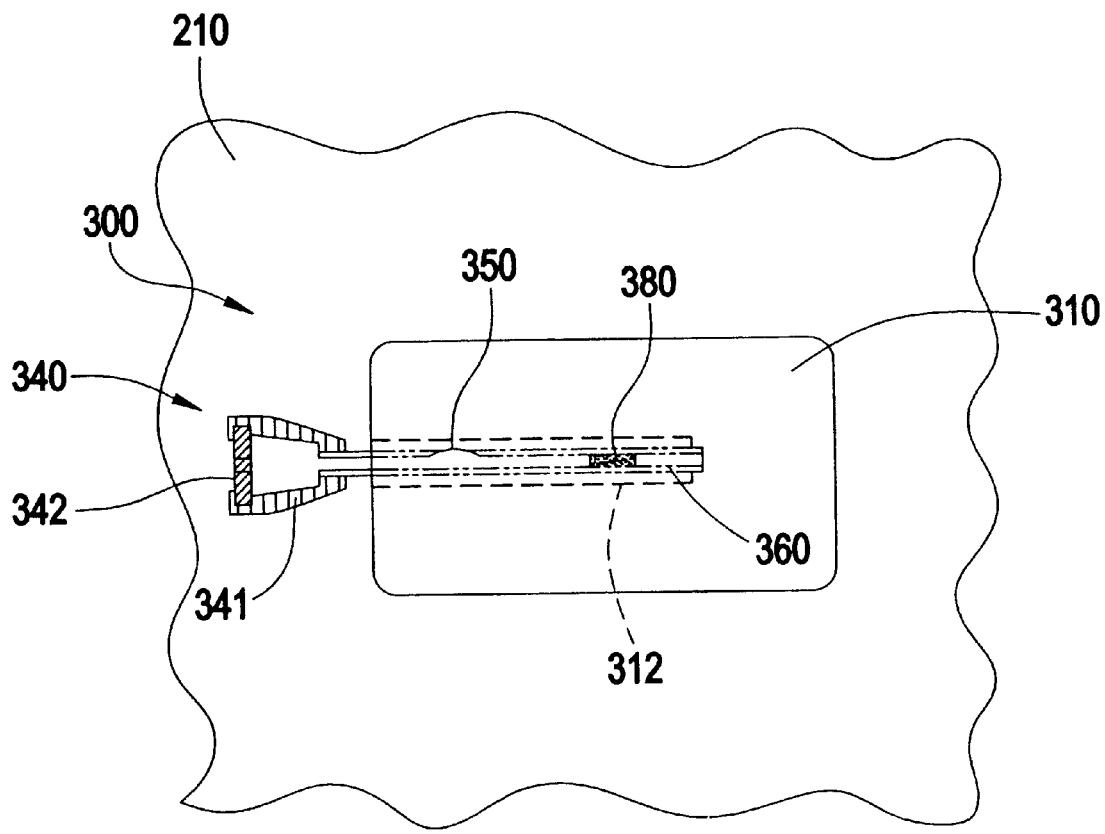
FIG. 32 is a top view, partially in section, of the device of FIG. 29, shown with the penetrating member removed.
Figure 33:
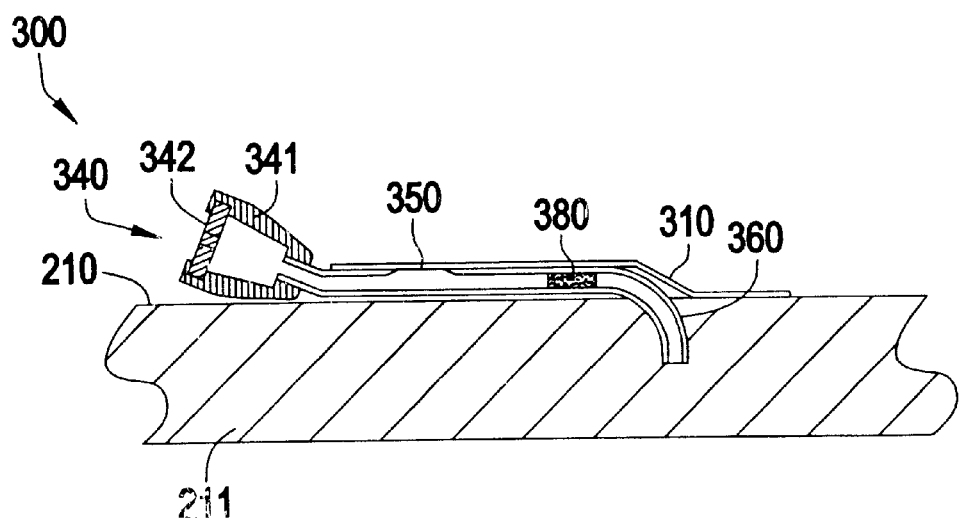
FIG. 33 is a sectional view of the device of FIG. 29 shown with the cannula remaining deployed in the subcutaneous tissue.

After the subcutaneous cannula 360 is inserted into the patient, the penetrator member 320 is removed from the device 300. Then the portion of the fluid delivery device 300 exiting the patient 900 is folded over so that the adhesive side of the skin patch 310 contacts the surface of the patient's skin 210 and fixedly attaches the device 300 to the patient 900 with the injector hub 340 exposed for receiving a needle and the distal tip of the subcutaneous cannula 360 secured in place in the subcutaneous tissue 211 of the patient 900, as shown in FIGS. 32 and 33.

FIGS. 34 and 35 show another device 300 similar to the device of FIGS. 30 and 31, but further including an accumulator constraint 351 for limiting the overall expansion of the expandable accumulator 350 to a fixed volume defined by the accumulator constraint 351. The addition of the accumulator constraint 351 allows a user, such as a patient or doctor, to easily fill the fluid delivery device 300 with the same volume at each use by applying a nominal amount of force when filling, or simply to allow a maximum dose and lesser volume doses. FIG. 35 shows the injector septum 342 of the device 300 receiving a needle 910.

Although exemplary embodiments of the invention have been shown and described, many changes, modifications and substitutions may be made by those having ordinary skill in the art without necessarily departing from the spirit and scope of this invention. For example, some of the disclosed devices are shown with and without a retractable or removable transcutaneous penetrating member. Other devices are included with a needle penetrable entry port or a mechanical valve such as a Luer, to access the device. Some devices are shown with medication reservoirs that are prefilled, and reservoirs that can be filled by the caregiver, patient or other user. All of these particular embodiments, as well as others described hereinabove, including but not limited to construction and materials of construction of reservoirs, compliant sections and their construction, flow restricting elements and construction, addition of check valves to fluid paths, can be utilized on the various devices described hereinabove without departing from the spirit and scope of the described invention.

In addition, where this patent application has listed the steps of a method or procedure in a specific order, it may be possible or even expedient in certain circumstances to change the order in which some steps are performed, and it is intended that the particular steps of the method or procedure claims set forth hereinbelow not be construed as being order-specific unless such order specificity is expressly stated in the claim.

What is claimed is:

1. A device for delivering fluid to a patient, comprising:
   a fluid passageway including,
      a proximal fluid transport tube;
      a distal fluid transport tube;
      a tubular expansion member coupling the fluid transport tubes;
   a penetrating member positioned within the expansion member for axial movement between the fluid transport tubes, the penetrating member having a sharpened distal tip;
   a dispenser for causing fluid from a reservoir to flow to the proximal fluid transport tube;
   a housing containing the dispenser and the fluid passageway and including an exit port receiving the distal fluid transport tube; and
   a connecting member secured to the penetrating member, movable from an exterior of the housing, and arranged such that movement of the connecting member causes the distal tip of the penetrating member to move towards the distal fluid transport tube to an extended position or away from the distal fluid transport tube to a retracted position.

2. A device according to claim 1, wherein the penetrating member is a needle.

3. A device according to claim 1, wherein the penetrating member is hollow.

4. A device according to claim 1, wherein the penetrating member is solid.

5. A device according to claim 1, wherein the penetrating member is flexible.

6. A device according to claim 1, wherein the penetrating member is straight.

7. A device according to claim 1, wherein the penetrating member is curved.

8. A device according to claim 1, wherein the distal tip of the penetrating member is positioned within the housing when the penetrating member is in the retracted position.

9. A device according to claim 1, wherein the penetrating member and the fluid passageway are sized to allow fluid flow between the passageway and the penetrating member.

10. A device according to claim 1, wherein an outside diameter of the penetrating member is substantially equal to an inside diameter of the distal fluid transport tube.

11. A device according to claim 1, wherein at least a portion of an outside diameter of the penetrating member is greater than an inside diameter of the distal fluid transport tube.

12. A device according to claim 1, wherein the proximal fluid transport tube is attached to both the connecting member and the penetrating member.

13. A device according to claim 1, wherein the expansion member is attached to both the connecting member and the penetrating member.

14. A device according to claim 1, further comprising a lubricant on or near the outside surface of the penetrating member.

15. A device according to claim 1, further comprising a therapeutic agent on a surface of the distal fluid transport tube.

16. A device according to claim 15, wherein the therapeutic agent includes at least one of an antibiotic agent, an analgesic agent, and a topical anesthetic.

17. A device according to claim 1, wherein the distal fluid transport tube is flexible.

18. A device according to claim 1, wherein the distal fluid transport tube is rigid.

19. A device according to claim 1, wherein the proximal fluid transport tube is flexible.

20. A device according to claim 1, wherein the proximal fluid transport tube is rigid.

21. A device according to claim 1, wherein the connecting member is attached to the expansion member.

22. A device according to claim 1, wherein an inner diameter of the expansion member is greater than an outer diameter of the penetrating member.

23. A device according to claim 1, wherein an inner diameter of the distal fluid transport tube is greater than an outer diameter of the penetrating member.

24. A device according to claim 1, wherein the expansion member has a bellows-type construction.

25. A device according to claim 1, wherein an inner diameter of the expansion member substantially equals an outer diameter of the penetrating member.

26. A device according to claim 1, wherein the expansion member is connected to the proximal fluid transport tube through the connecting member.

27. A device according to claim 1, wherein the device is attachable to a patient's skin, and a direction of movement of the connecting member is substantially parallel to a surface of the skin.

28. A device according to claim 1, wherein movement of the connecting member in a first direction causes the penetrating member to move towards a distal end of the distal fluid transport tube and movement of the connecting member in a second direction causes the penetrating member to move away from the distal end of the distal fluid transport tube.

29. A device according to claim 28, wherein the connecting member is biased in the second direction.

30. A device according to claim 1, wherein the connecting member extends through the expansion member and is mechanically attached to the penetrating member.

31. A device according to claim 1, wherein the connecting member extends through the proximal fluid transport tube and is mechanically attached to the penetrating member.

32. A device according to claim 1, wherein the connecting member is connected to the penetrating member through one of the proximal fluid transport tube, the expansion member, and distal fluid transport tube.

33. A device according to claim 1, further comprising a reservoir, and the dispenser controls fluid flow from the reservoir to the proximal fluid transport tube.

34. A device according to claim 33, wherein the reservoir contains a therapeutic fluid.

35. A device according to claim 33, wherein the reservoir is pressurized.

36. A device according to claim 1, further comprising:
   a local processor connected to the dispenser and programmed to cause the dispenser to allow fluid flow from a reservoir to the proximal fluid transport tube based on flow instructions;
   a wireless receiver connected to the local processor for receiving flow instructions from a separate, remote control device and delivering the flow instructions to the local processor; and
   wherein the housing is free of user input components for providing flow instructions to the local processor.

37. A system including a fluid delivery device according to claim 36, and further comprising a remote control device separate from the fluid delivery device and including:
   a remote processor;
   user interface components connected to the remote processor for allowing a user to provide flow instructions to the remote processor; and
   a transmitter connected to the remote processor for transmitting the flow instructions to the receiver of the fluid delivery device.

38. A device according to claim 1, further comprising:
   a local processor connected to the dispenser and programmed to cause the dispenser to allow fluid flow from a reservoir to the proximal fluid transport tube based on flow instructions, and further programmed to provide flow information;
   a wireless transmitter connected to the local processor for transmitting the flow information from the local processor to a separate, remote control device; and
   wherein the housing is free of user output components for providing the flow information from the local processor to a user.

39. A system including a fluid delivery device according to claim 38 and further comprising a remote control device separate from the fluid delivery device and including:
   a remote processor;
   user output components connected to the remote processor for allowing a user to receive flow information; and
   a receiver connected to the remote processor for receiving the flow information from the transmitter of the fluid delivery device.

40. A device according to claim 1, further comprising an adhesive layer on an outer surface of the housing.

41. A device according to claim 1, wherein the exit port includes an elongated bore receiving and supporting the distal fluid transport tube.

* * * * *